(12) United States Patent
Kaufmann et al.

(10) Patent No.: US 10,098,755 B2
(45) Date of Patent: Oct. 16, 2018

(54) STAND ALONE INTERBODY SPINAL SYSTEM

(71) Applicant: Genesys Spine, Austin, TX (US)

(72) Inventors: Joshua Kaufmann, Austin, TX (US); Greg Calbert, Austin, TX (US); Scott Bryant, Austin, TX (US); Brian Bergeron, Austin, TX (US); Landon Gilkey, Austin, TX (US); Ben Keller, Austin, TX (US); Bernard H. Guiot, Denver, CO (US); Aizik Wolf, Miami, FL (US); Matthew Philips, Dartmouth, MA (US); John T. Friedland, Destin, FL (US)

(73) Assignee: Genesys Spine, Austin, TX (US)

( * ) Notice: Subject to any disclaimer, the term of this patent is extended or adjusted under 35 U.S.C. 154(b) by 0 days.

(21) Appl. No.: 15/605,334

(22) Filed: May 25, 2017

(65) Prior Publication Data
US 2017/0340453 A1 Nov. 30, 2017

Related U.S. Application Data

(60) Provisional application No. 62/445,428, filed on Jan. 12, 2017, provisional application No. 62/341,123, filed on May 25, 2016.

(51) Int. Cl.
*A61F 2/44* (2006.01)
*A61F 2/46* (2006.01)
*A61F 2/30* (2006.01)

(52) U.S. Cl.
CPC .......... *A61F 2/4455* (2013.01); *A61F 2/4611* (2013.01); *A61F 2002/30016* (2013.01);
(Continued)

(58) Field of Classification Search
CPC .. A61F 2/44; A61F 2/4455; A61F 2/46; A61F 2/4611; A61F 2/30
See application file for complete search history.

(56) References Cited

U.S. PATENT DOCUMENTS

| 6,342,074 B1 | 1/2002 | Simpson |
| 6,447,546 B1 | 9/2002 | Bramlet et al. |

(Continued)

OTHER PUBLICATIONS

The International Searching Authority, "Notification of Transmittal of the International Search Report and Written Opinion," dated Sep. 4, 2017 in International Application No. PCT/US2017/034471.

*Primary Examiner* — Christopher Beccia
(74) *Attorney, Agent, or Firm* — Trop, Pruner & Hu, P.C.

(57) ABSTRACT

An embodiment includes an orthopedic fusion system comprising: a cage; a curved first channel coupling a lateral wall of the cage to a superior surface of the cage; a curved second channel coupling the lateral wall of the cage to an inferior surface of the cage; a third channel coupling the superior surface of the cage to the inferior surface of the cage; a curved first anchor configured to slide within the first channel; a curved second anchor configured to slide within the second channel; and a resilient member comprising a resilient first arm that projects across a portion of the first channel and a resilient second arm that projects across a portion of the second channel. Other embodiments are described herein.

20 Claims, 30 Drawing Sheets

(52) U.S. Cl.
CPC ............... *A61F 2002/30579* (2013.01); *A61F 2002/30622* (2013.01); *A61F 2002/4619* (2013.01); *A61F 2002/4628* (2013.01); *A61F 2002/4629* (2013.01)

(56) References Cited

U.S. PATENT DOCUMENTS

| | | | |
|---|---|---|---|
| 7,594,931 B2 | 9/2009 | Louis et al. | |
| 7,695,516 B2 | 4/2010 | Zeegers | |
| 8,147,556 B2 | 4/2012 | Louis et al. | |
| 8,328,872 B2 | 12/2012 | Duffield et al. | |
| 8,343,219 B2 | 1/2013 | Allain et al. | |
| 8,460,385 B1 * | 6/2013 | Wensel | A61B 17/864 623/17.11 |
| 8,641,768 B2 | 2/2014 | Duffield et al. | |
| D712,036 S | 8/2014 | Davenport | |
| 8,808,304 B2 | 8/2014 | Weiman et al. | |
| 9,044,337 B2 | 6/2015 | Dinville et al. | |
| 9,060,808 B2 | 6/2015 | Overes et al. | |
| 9,173,745 B2 | 11/2015 | Dinville et al. | |
| 9,173,750 B2 | 11/2015 | Weiman et al. | |
| 9,333,095 B2 | 5/2016 | Beaurain et al. | |
| 9,364,343 B2 | 6/2016 | Duffield et al. | |
| 9,517,144 B2 | 12/2016 | McAtamney et al. | |
| 9,775,722 B2 | 10/2017 | Kim et al. | |
| 2010/0204739 A1 | 8/2010 | Bae et al. | |
| 2012/0116466 A1 | 5/2012 | Dinville et al. | |
| 2012/0130496 A1 | 5/2012 | Duffield et al. | |
| 2012/0130497 A1 | 5/2012 | Taylor | |
| 2012/0191196 A1 | 7/2012 | Louis et al. | |
| 2012/0277870 A1 * | 11/2012 | Wolters | A61F 2/447 623/17.16 |
| 2013/0060339 A1 | 3/2013 | Duffield et al. | |
| 2013/0150968 A1 | 6/2013 | Dinville et al. | |
| 2013/0226300 A1 | 8/2013 | Chataigner et al. | |
| 2015/0051702 A1 | 2/2015 | Chataigner et al. | |
| 2015/0051704 A1 | 2/2015 | Duffield et al. | |
| 2015/0127107 A1 | 5/2015 | Kim et al. | |
| 2015/0209089 A1 | 7/2015 | Chataigner et al. | |
| 2015/0305887 A1 * | 10/2015 | McAtamney | A61F 2/4455 623/17.16 |
| 2015/0320568 A1 | 11/2015 | Ameil et al. | |
| 2016/0100953 A1 | 4/2016 | Dinville et al. | |
| 2016/0242930 A1 | 8/2016 | Duffield et al. | |
| 2016/0324652 A1 | 11/2016 | Brow | |
| 2017/0042692 A1 | 2/2017 | Stewart et al. | |
| 2017/0056198 A1 | 3/2017 | Ameil et al. | |
| 2017/0246007 A1 | 8/2017 | Chataigner et al. | |
| 2017/0246008 A1 | 8/2017 | Mercier et al. | |
| 2017/0311997 A1 | 11/2017 | Lequette et al. | |

* cited by examiner

US 10,098,755 B2

STAND ALONE INTERBODY SPINAL SYSTEM

PRIORITY CLAIM

This application claims priority to: (a) U.S. Provisional Patent Application No. 62/445,428, filed on Jan. 12, 2017 and entitled "Stand Alone Interbody Spinal System", and (b) U.S. Provisional Patent Application No. 62/341,123, filed on May 25, 2016 and entitled "Stand Alone Interbody Spinal System". The content of each of the above applications is hereby incorporated by reference.

TECHNICAL FIELD

Embodiments of the invention are in the field of orthopedic implants.

BACKGROUND

Fixation devices can be used to provide, for example, immobilization and stabilization of spinal segments in patients (e.g., humans, dogs, cats, and other animals). Fixation devices may be used to help fuse bone segments (e.g., vertebrae) in the treatment of instabilities or deformities of, for example, the cervical, thoracic, lumbar, and/or sacral spine. Such instabilities or deformities may include, for example, degenerative disc disease (DDD); spondylolisthesis; trauma (i.e., fracture or dislocation); spinal stenosis; curvatures (i.e., scoliosis, kyphosis, and/or lordosis); tumor; pseudoarthrosis; and failed previous fusions.

One such fixation device may include an interbody spacer implanted using techniques such as Anterior Lumbar Interbody Fusion (ALIF), Posterior Lumbar Interbody Fusion (PLIF), or Transforaminal Lumbar Interbody Fusion (TLIF) surgical techniques. The spacers used in these techniques are placed in the interdiscal space between adjacent vertebrae of the spine. Many times an exterior plate is used in conjunction with the spacer to hold the adjacent vertebrae while the fusion occurs.

Ideally, the spacer should stabilize the intervertebral space and allow fusion of the adjacent vertebrae. Moreover, during the time it takes for fusion to occur, the interbody spacer should have sufficient structural integrity to withstand the stress of maintaining the space without substantially degrading or deforming and have sufficient stability to remain securely in place prior to actual bone ingrowth fusion.

The degree or success of union, loads produced by weight bearing, and activity levels will, among other conditions, dictate the longevity of the implant. Robust fixation systems are needed to lessen risks associated with fixation and to promote better outcomes for patients.

BRIEF DESCRIPTION OF THE DRAWINGS

Features and advantages of embodiments of the present invention will become apparent from the appended claims, the following detailed description of one or more example embodiments, and the corresponding figures, in which:

DETAILED DESCRIPTION

In the following description, numerous specific details are set forth. However, it is understood that embodiments of the invention may be practiced without these specific details. Well-known structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features described for other embodiments. Also, as used herein "first", "second", "third" and the like describe a common object and indicate that different instances of like objects are being referred to. Such adjectives are not intended to imply the objects so described must be in a given sequence, either temporally, spatially, in ranking, or in any other manner. Also, the terms "coupled" and "connected," along with their derivatives, may be used. In particular embodiments, "connected" may be used to indicate that two or more elements are in direct physical contact with each other and "coupled" may mean that two or more elements co-operate or interact with each other, but they may or may not be in direct physical contact.

Figure 11:
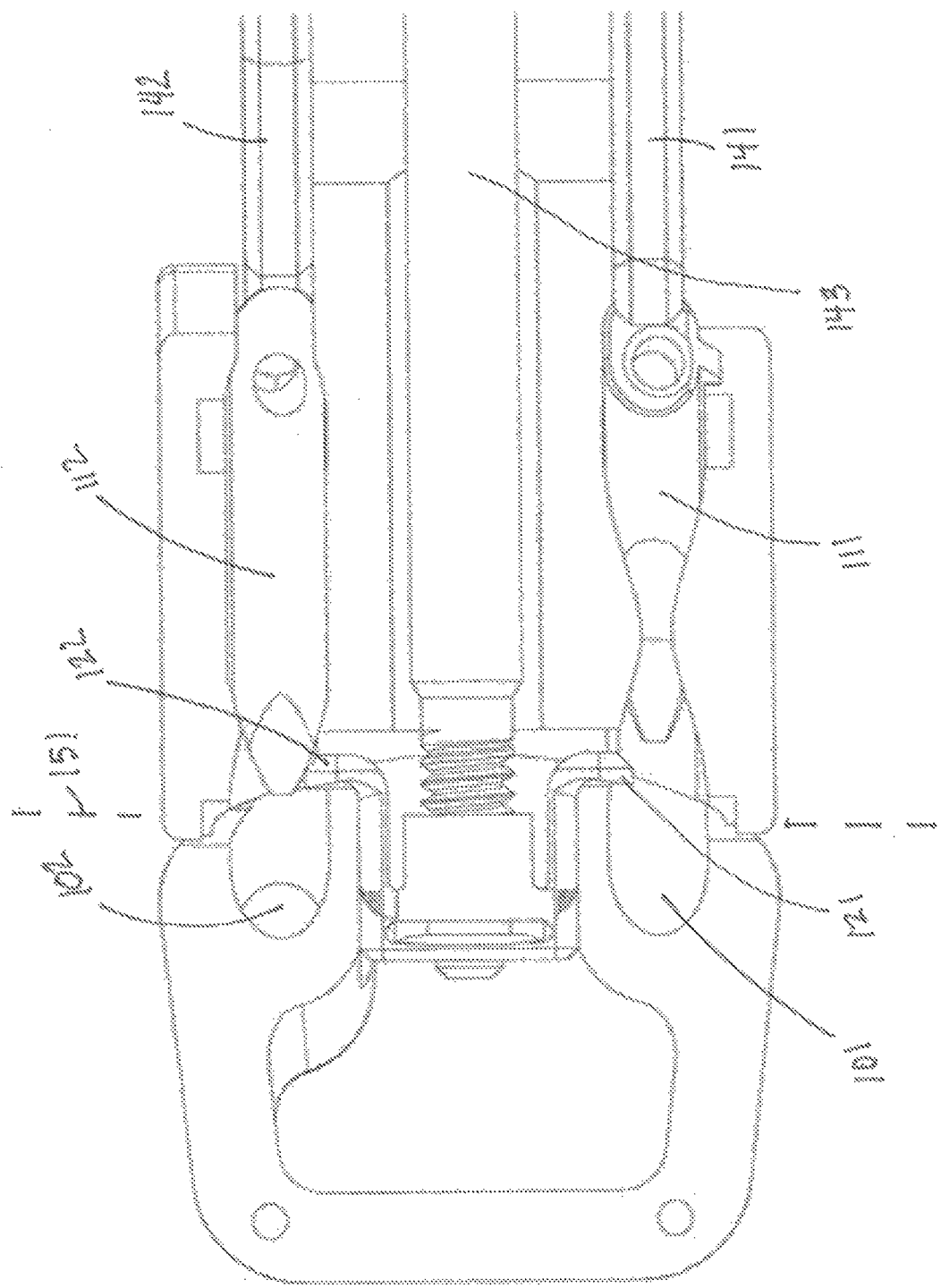
FIGS. 11, 12, 13 include cross-sectional views of an embodiment of a standalone interbody cage, anchors, and insertion tool at various points of anchor deployment within a channel of the cage.

FIGS. 1 to 6 and 11 are now discussed. Those figures depict an orthopedic fusion system 100 comprising: a cage 110; a curved first channel 101 coupling a lateral wall 130 of the cage to a superior surface 131 of the cage; a curved second channel 102 coupling the lateral wall of the cage to an inferior surface 132 of the cage; a third channel 103 coupling the superior surface of the cage to the inferior surface of the cage; a curved first anchor 111 configured to slide within the first channel; a curved second anchor 112 configured to slide within the second channel; and a resilient member 120 comprising a resilient first arm 121 that projects across a portion of the first channel and a resilient second arm 122 that projects across a portion of the second channel. FIG. 11 also shows first arm 121 projecting across a portion of the first channel 101 and second arm 122 projecting across a portion of the second channel 102.

Figure 4:
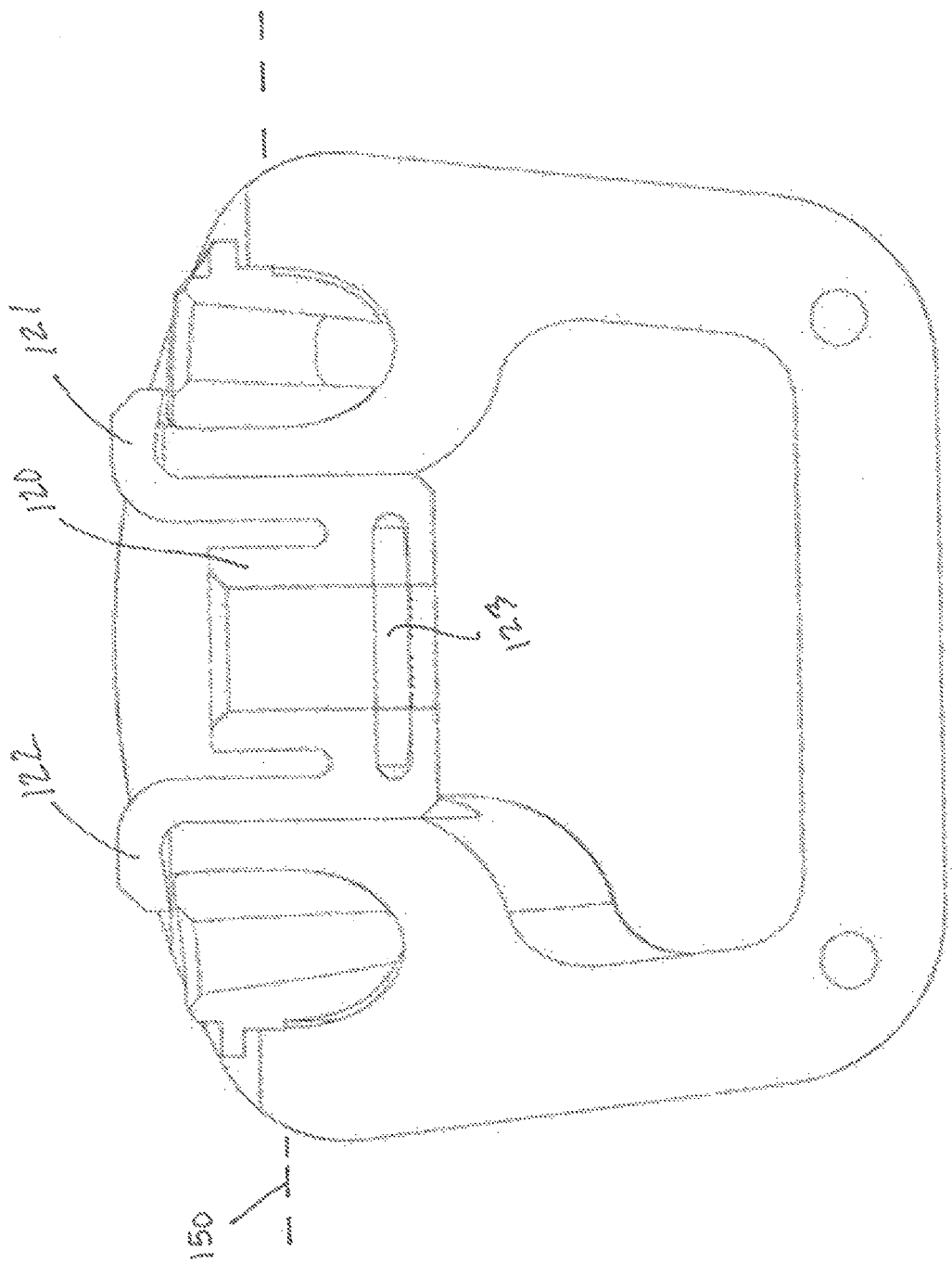
FIG. 4 includes a cross-sectional view of an embodiment of a standalone interbody cage and anchors.
Figure 5:
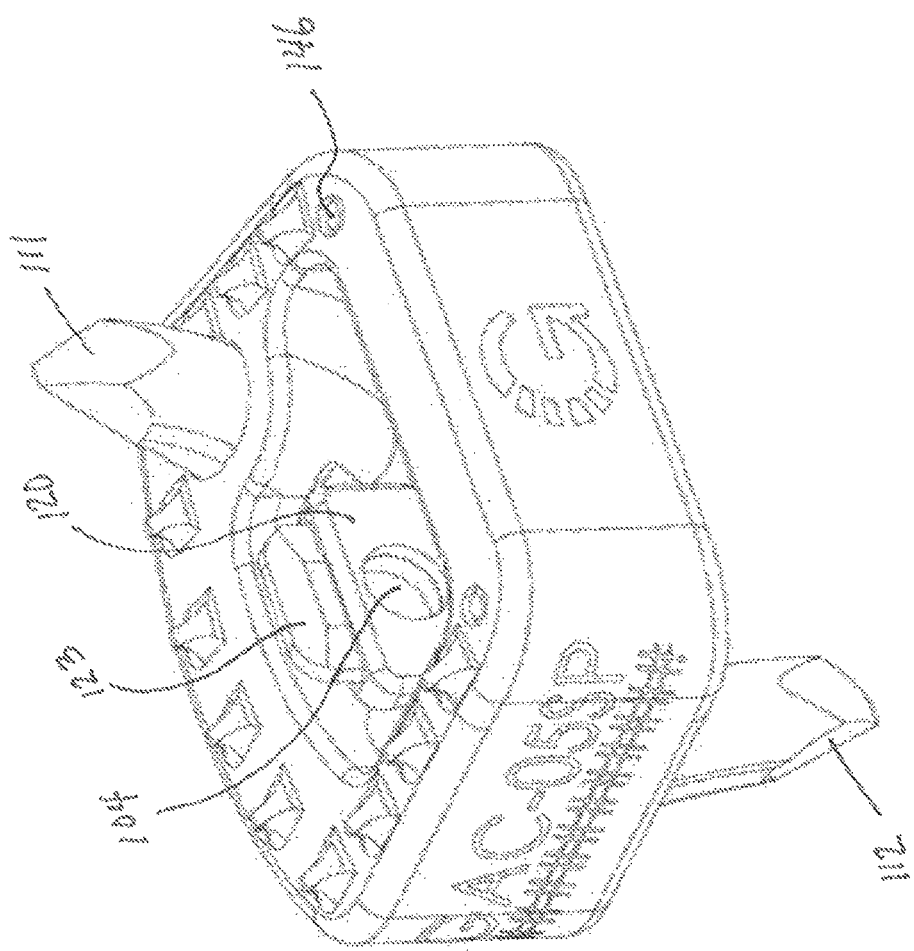
FIG. 5 includes a perspective view of an embodiment of a standalone interbody cage and anchors.
Figure 6:
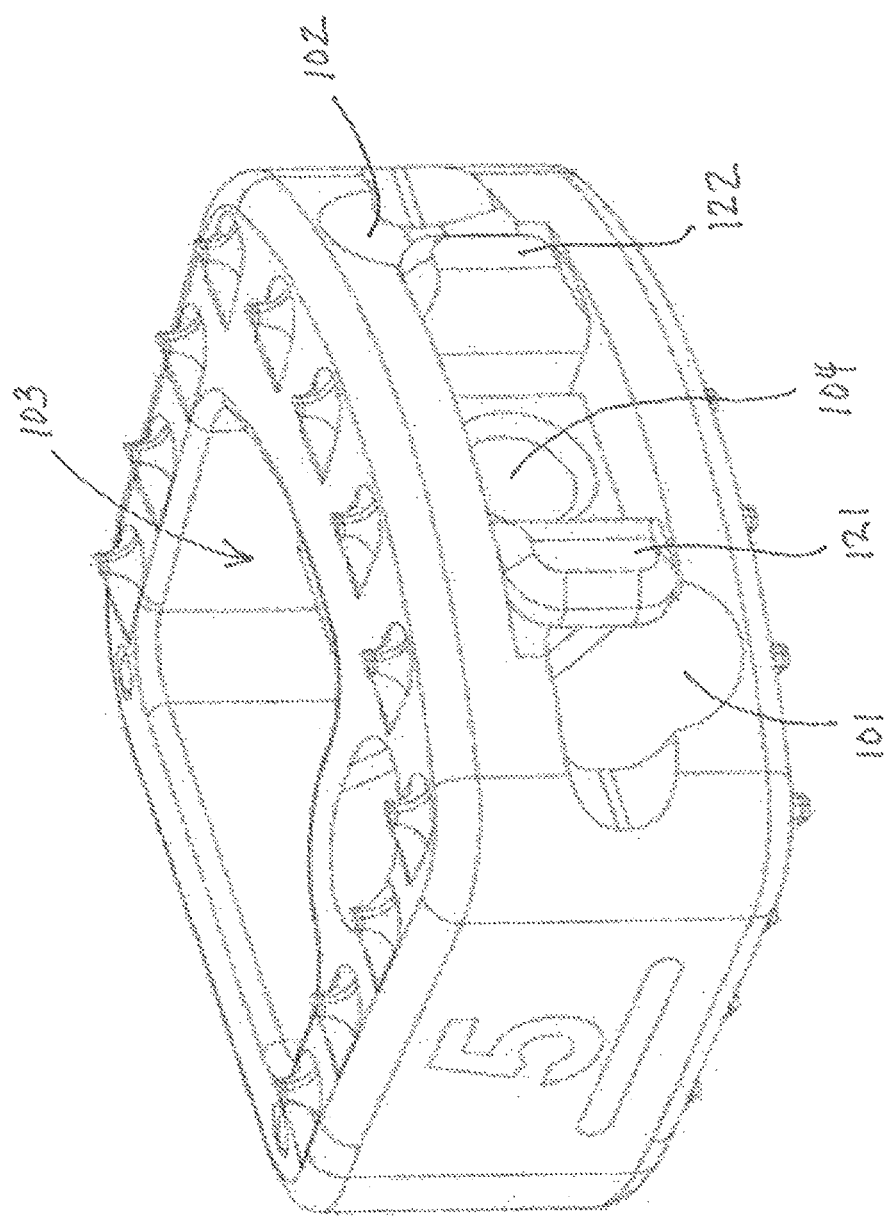
FIG. 6 includes a perspective view of an embodiment of a standalone interbody cage.

In an embodiment the first and second arms 121, 122 are monolithic with one another. For example, see FIG. 4 showing member 120 as being a monolithic structure comprising a base that couples arms 121, 122 to each other. Structure 120 may couple to another retention member 123 (FIG. 5) that is not necessarily monolithic with the arms. Thus, arms 121, 122 prevent structure 120 from advancing too far into channel 103 and member 123 keeps member 120 from backing out of cage 110.

Figure 12:
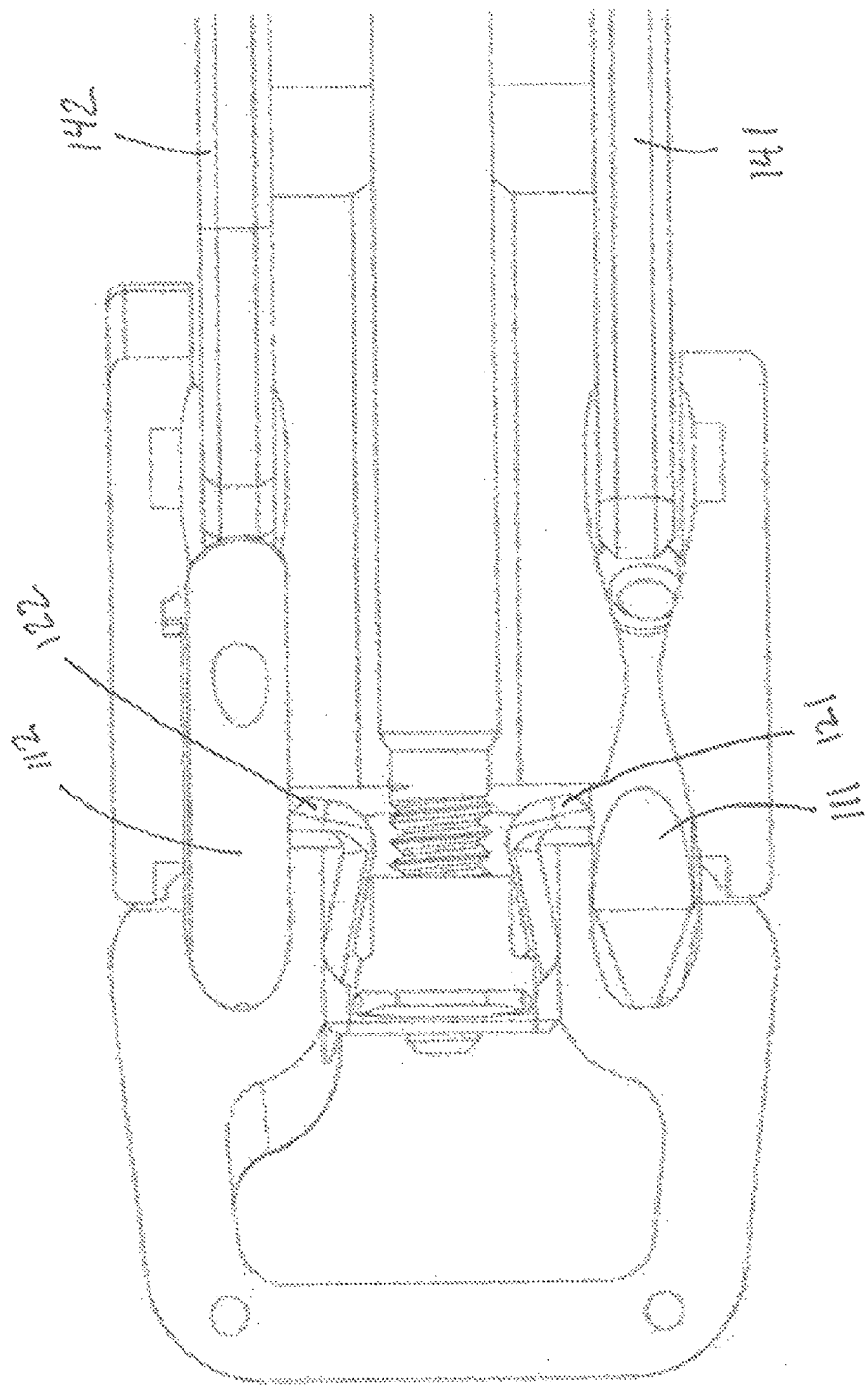
Figure 13:
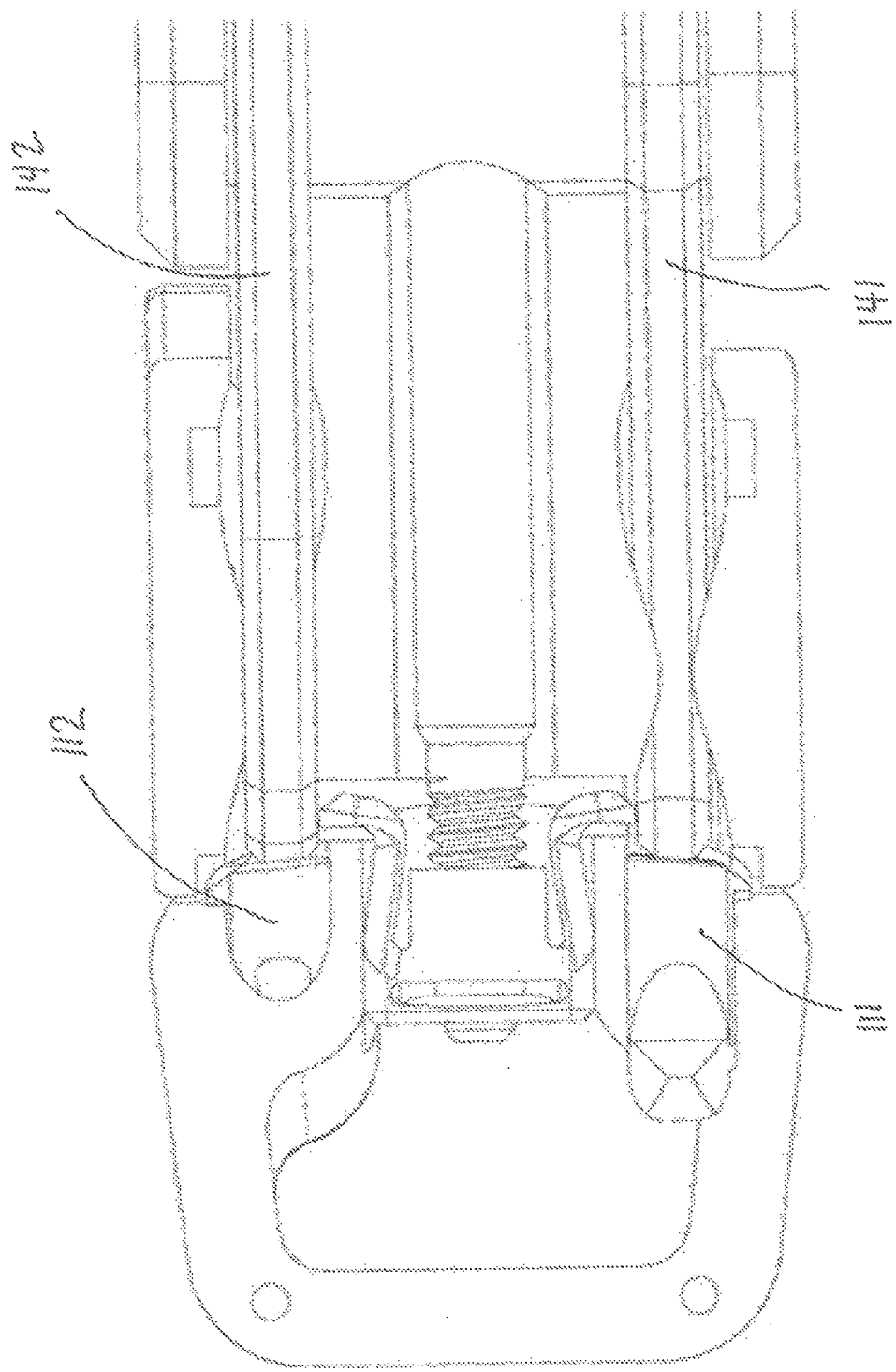
Figure 14:
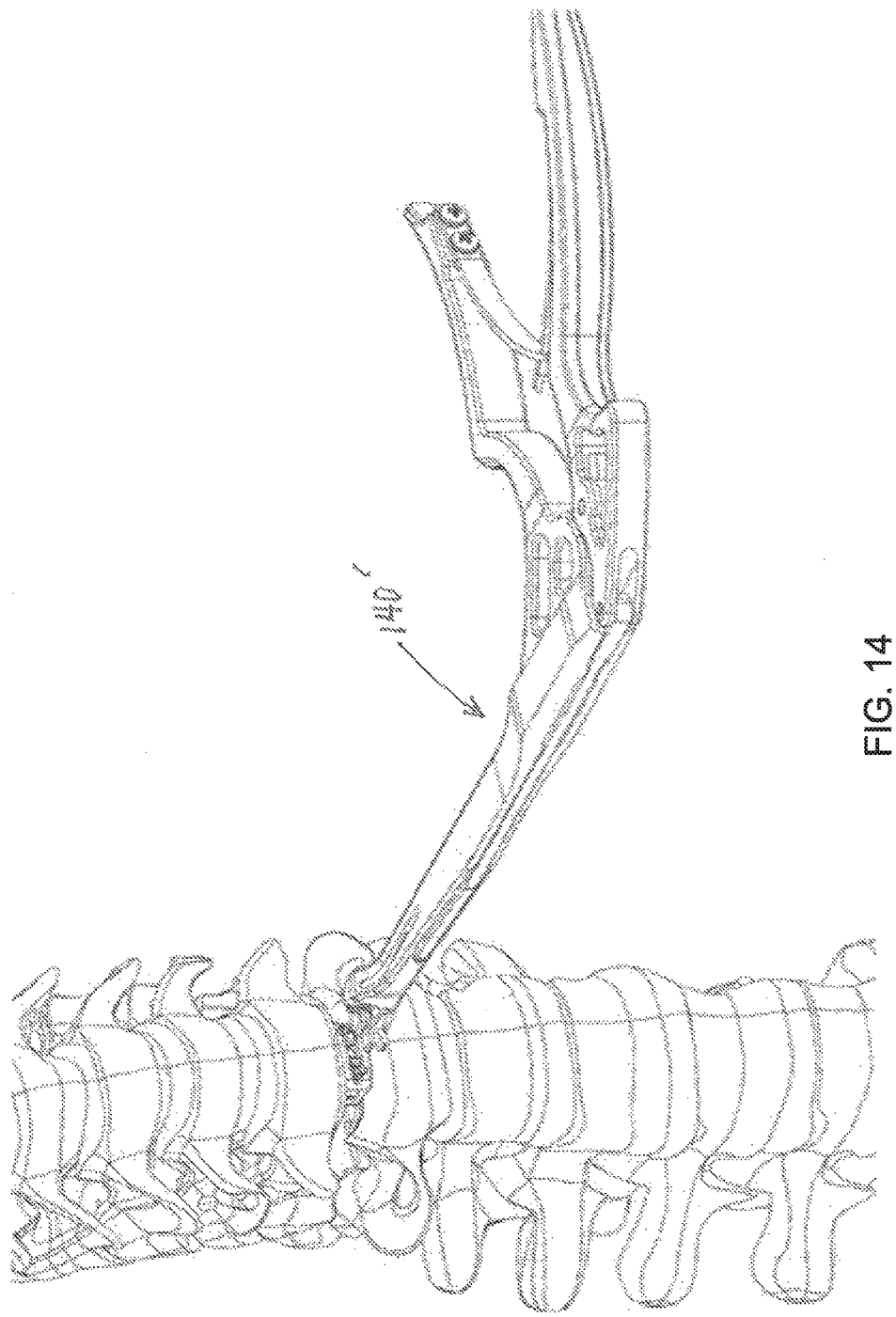
FIGS. 14, 15, 16, 17, 18 include perspective views of an embodiment of a standalone interbody cage and withdrawal tool at various points of anchor withdrawal from a channel of the cage.
Figure 15:
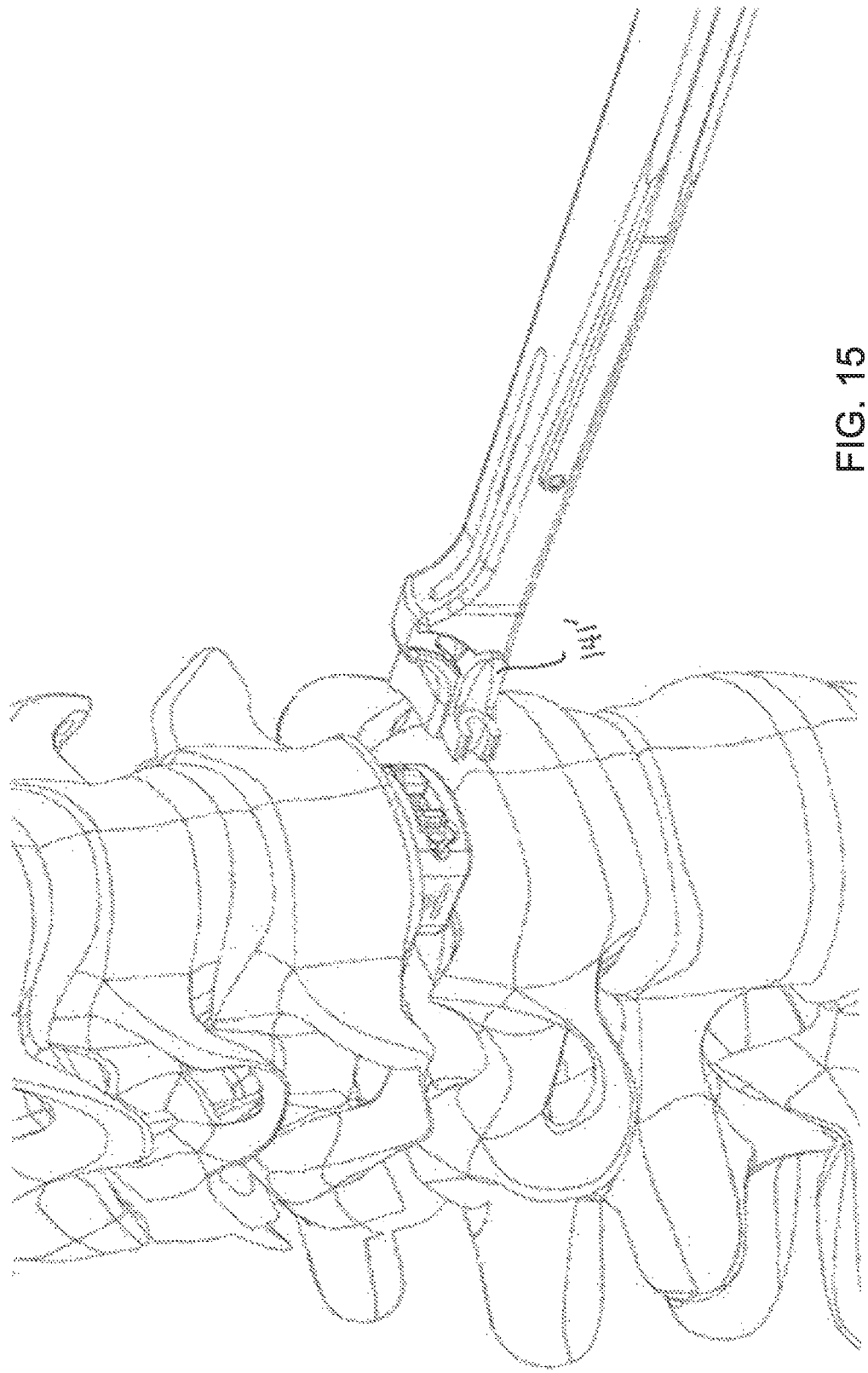

FIGS. 8 to 13 show various views and stages of implantation of anchors. FIG. 12 shows where in a first orientation the first anchor 111 directly deflects the first arm 121 away from the first channel (first channel 101 is more easily seen in FIG. 11) to allow the first anchor 111 to pass within the first channel. In the first orientation (FIG. 12) the second anchor 112 directly deflects the second arm 122 away from the second channel (second channel 102 is more easily seen in FIG. 11) to allow the second anchor to pass within the second channel. Thus, in an embodiment the first and second anchors are configured to deploy into the first and second channels "simultaneously" (as define below) with one another.

Figure 7:
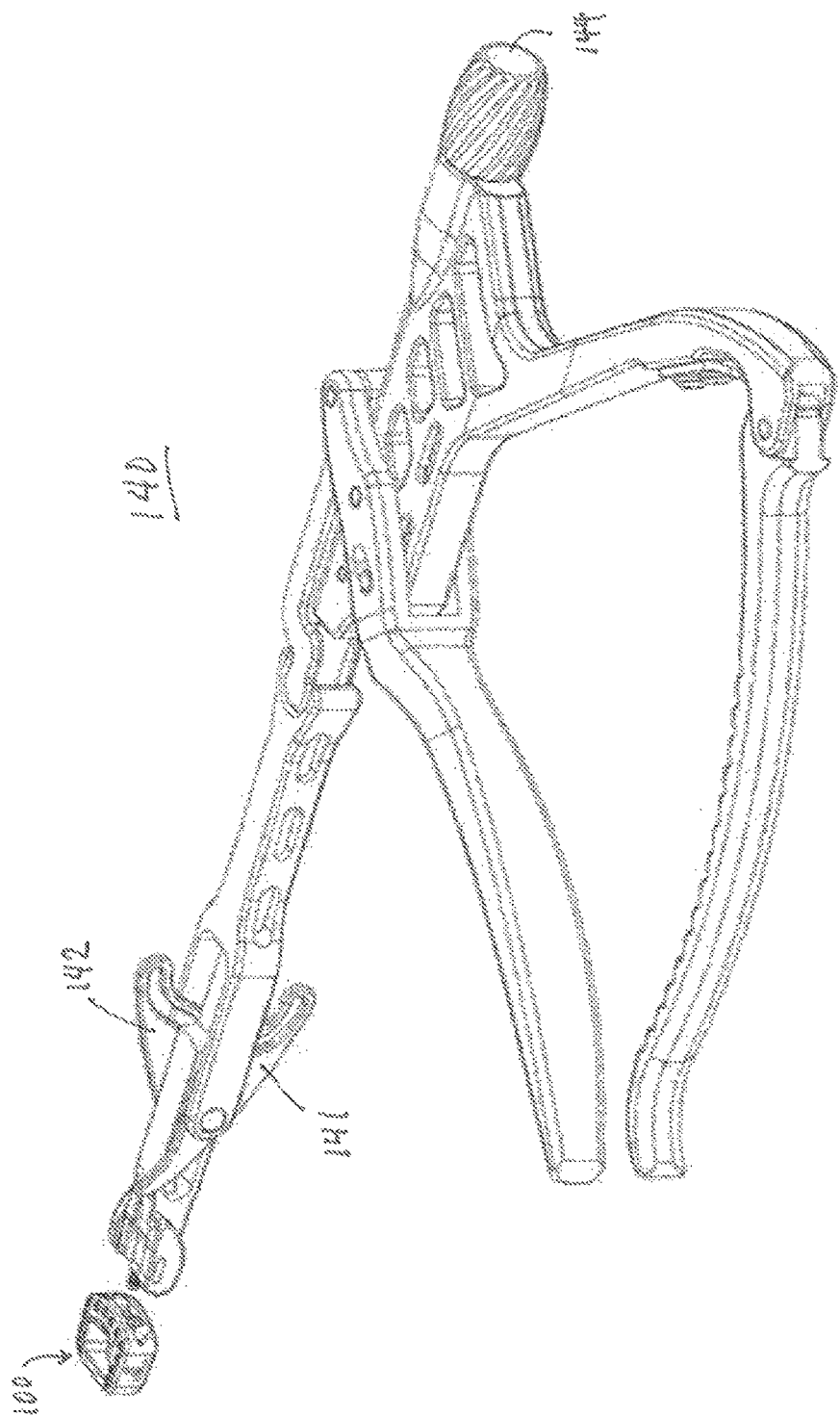
FIG. 7 includes a perspective view of an embodiment of a standalone interbody cage, anchors, and insertion tool.
Figure 8:
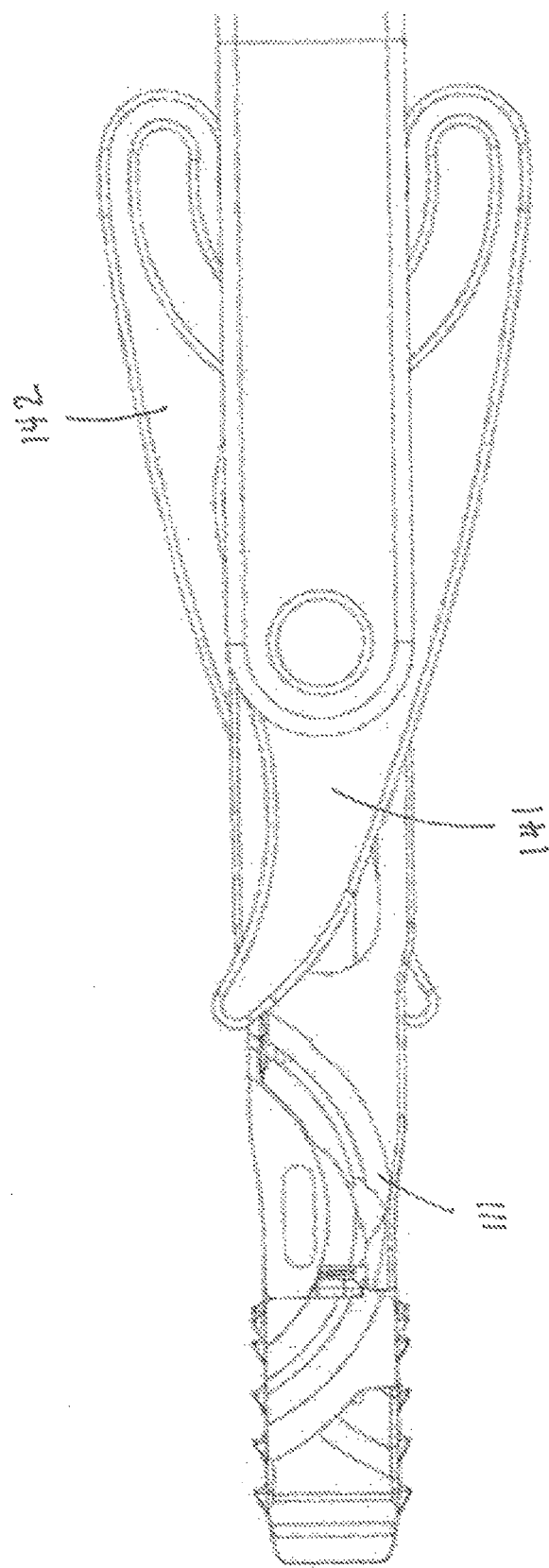
FIGS. 8, 9, 10 include cross-sectional views of an embodiment of a standalone interbody cage, anchors, and insertion tool at various points of anchor deployment within a channel of the cage.
Figure 9:
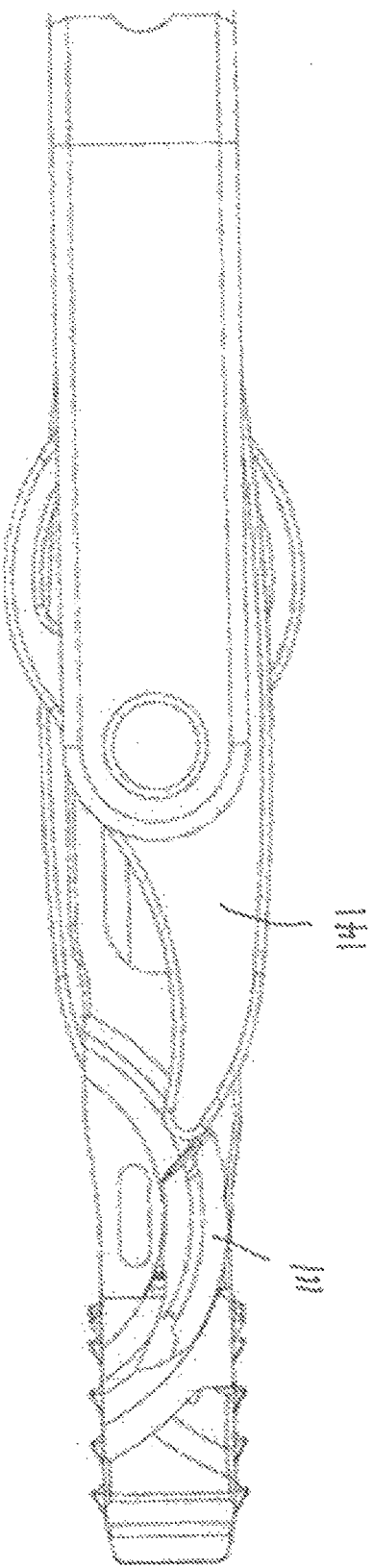
Figure 27:
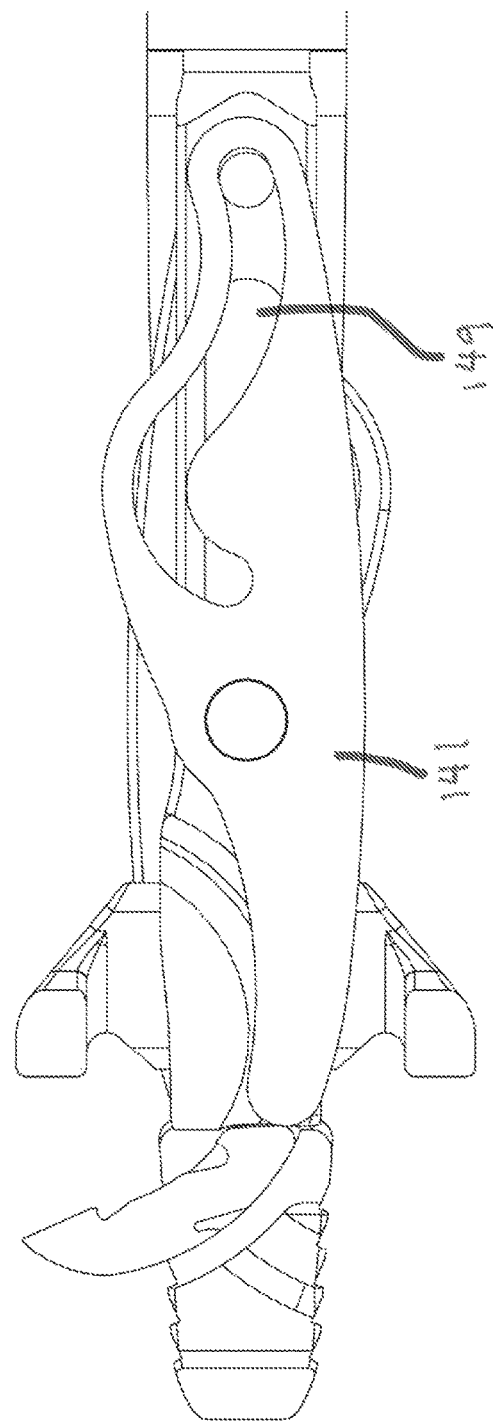
FIG. 27 includes an insertion tool in an embodiment.

FIG. 7 depicts an insertion tool 140, the insertion tool comprising: a first insertion tool arm 141 configured to travel along a first arcuate path (see path taken in FIGS. 8, 9, 10) to drive the first anchor 111 along the first channel 101; a second insertion tool arm 142 configured to travel along a second arcuate path (see path taken in FIGS. 8, 9, 10) to drive the second anchor 112 along the second channel 102. Accordingly, the first and second insertion tool arms are configured to respectively travel along the first and second arcuate paths simultaneously with one another. As a result, a patient benefits because simultaneous anchor insertion saves procedure time. FIG. 27 shows how an arcuate path (including undulating portions) may be due in part to a serpentine channel 149 on an arm, such as arm 141. Not all paths for insertion arms must be arcuate (as used herein arcuate means "curved") and may be, for example, linear in other embodiments.

Figure 1:
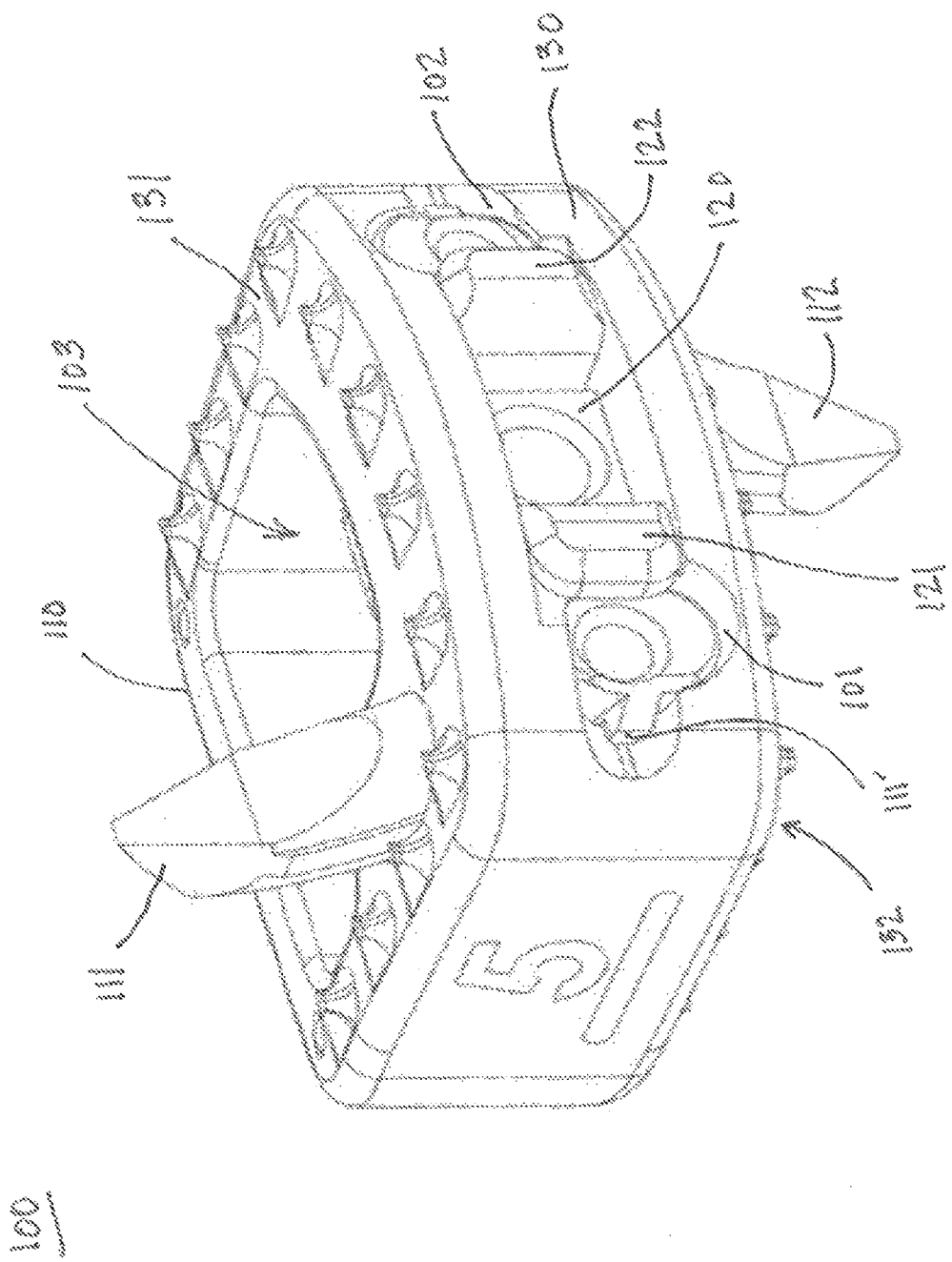
FIG. 1 includes a perspective view of an embodiment of a standalone interbody cage and anchors.
Figure 2:
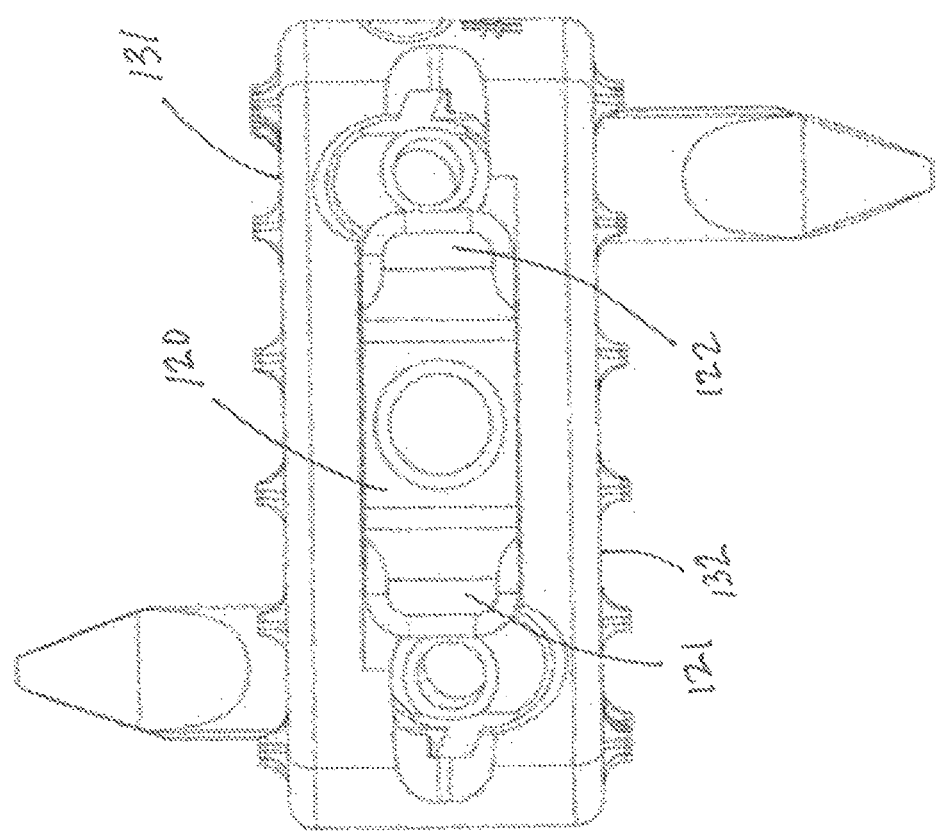
FIG. 2 includes a side view of an embodiment of a standalone interbody cage and anchors.
Figure 3:
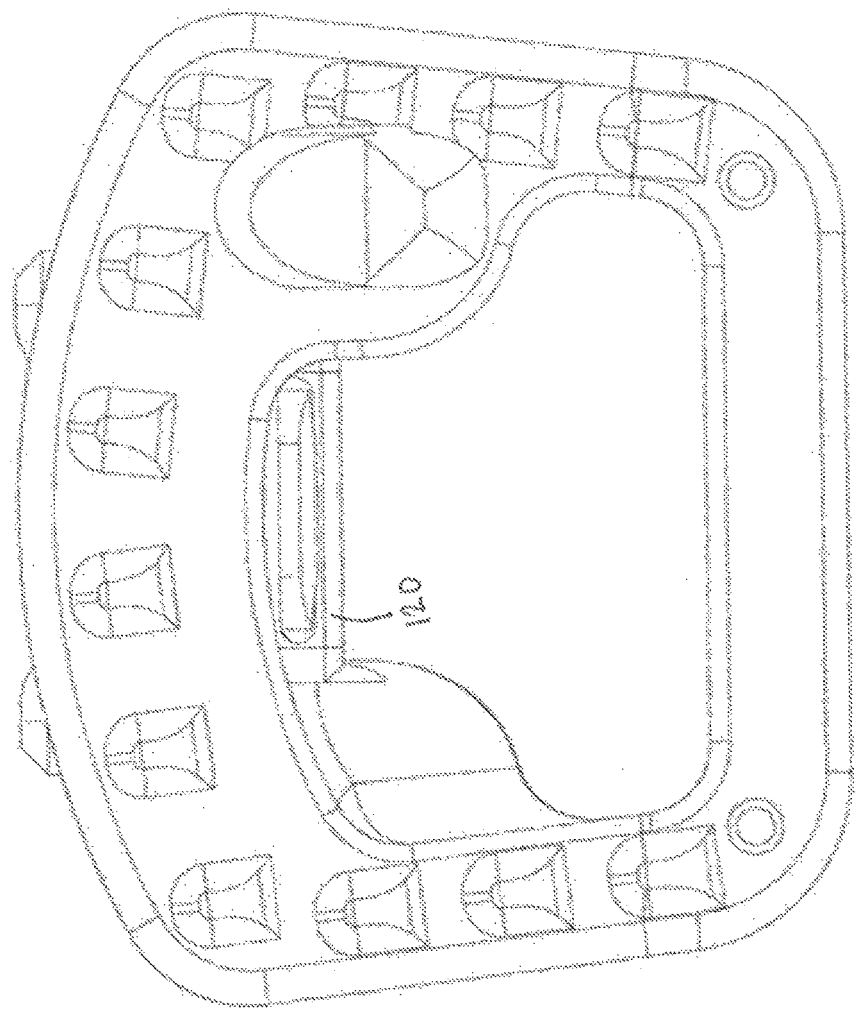
FIG. 3 includes a top view of an embodiment of a standalone interbody cage and anchors.

As shown in FIGS. 1, 2, 4, after anchor insertion the system may enter into a second orientation. In a second orientation: (a) a portion of the first arm 121 is lateral to a proximal end of the first anchor 111 and prevents the first anchor from backing out of the first channel 101, and (b) the first anchor does not deflect the first arm away from the first channel.

Figure 10:
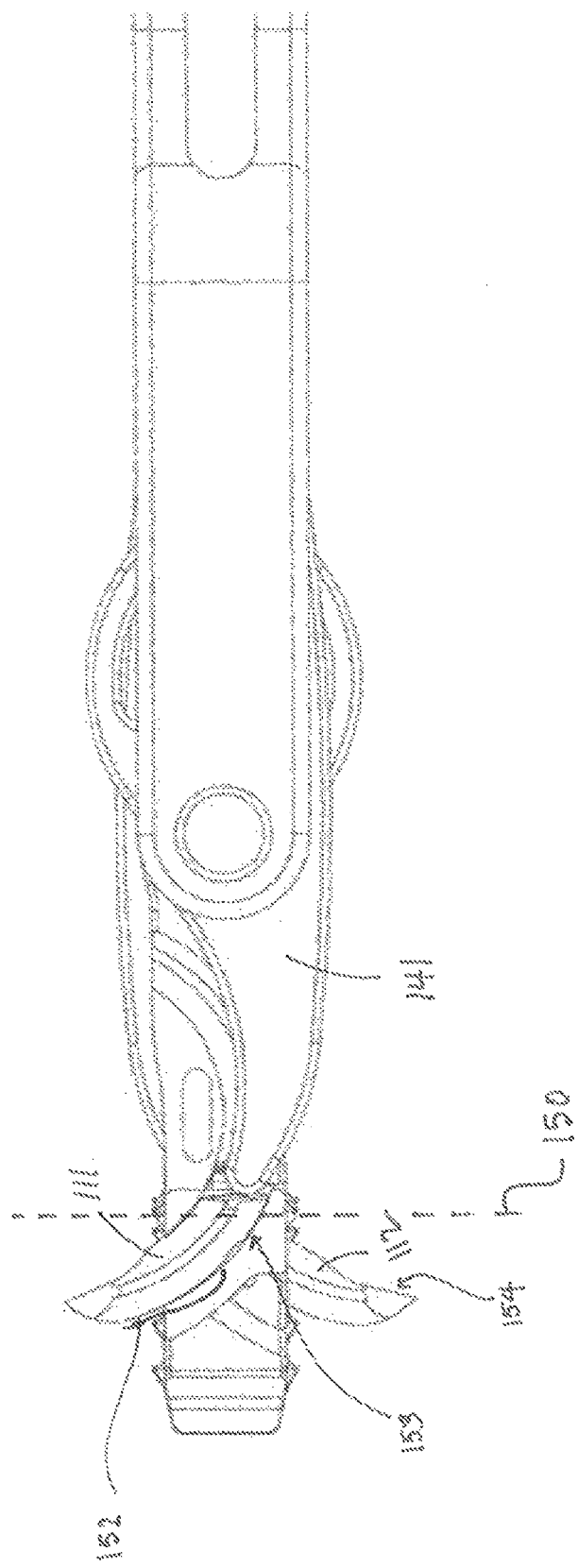

FIG. 10 shows (indirectly) how in a vertical plane 150 the first anchor 111 is completely surrounded by an interior wall of the first channel 101. Actually, FIG. 10 shows how anchor 111 is surrounded on two sides (top and bottom) by the channel wall. FIG. 4 helps show how anchor 111 is surrounded on two additional sides (left and right sides) by the channel wall (with all four sides shown in FIGS. 10 and 4 amounting to "surrounding" as used herein). In an embodiment a horizontal axis 151 (FIG. 11) intersects the lateral wall and the first and second channels. In an embodiment a horizontal axis 151 (FIG. 11) intersects the lateral wall and the first and second channels and the resilient member 120.

In FIG. 1 the first anchor 111 includes a projection 111' configured to abut a wall of the first channel 101 to prevent a proximal portion (wherein the "proximal end" of anchor 111 is the opposite end of anchor from the pointed distal tip projecting superiorly in FIG. 1) of the first anchor 111 from passing through the first channel.

Figure 16:
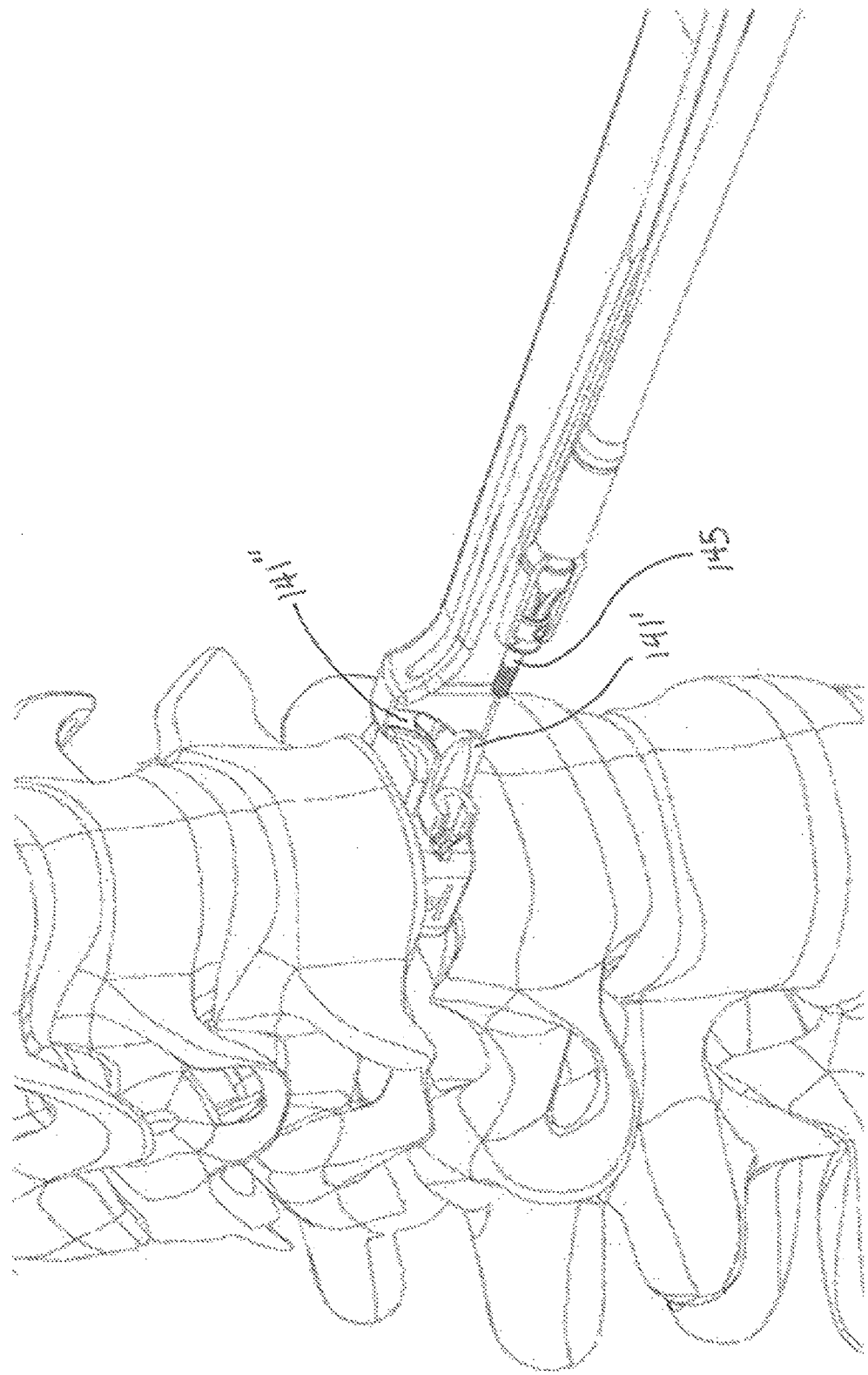
Figure 17:
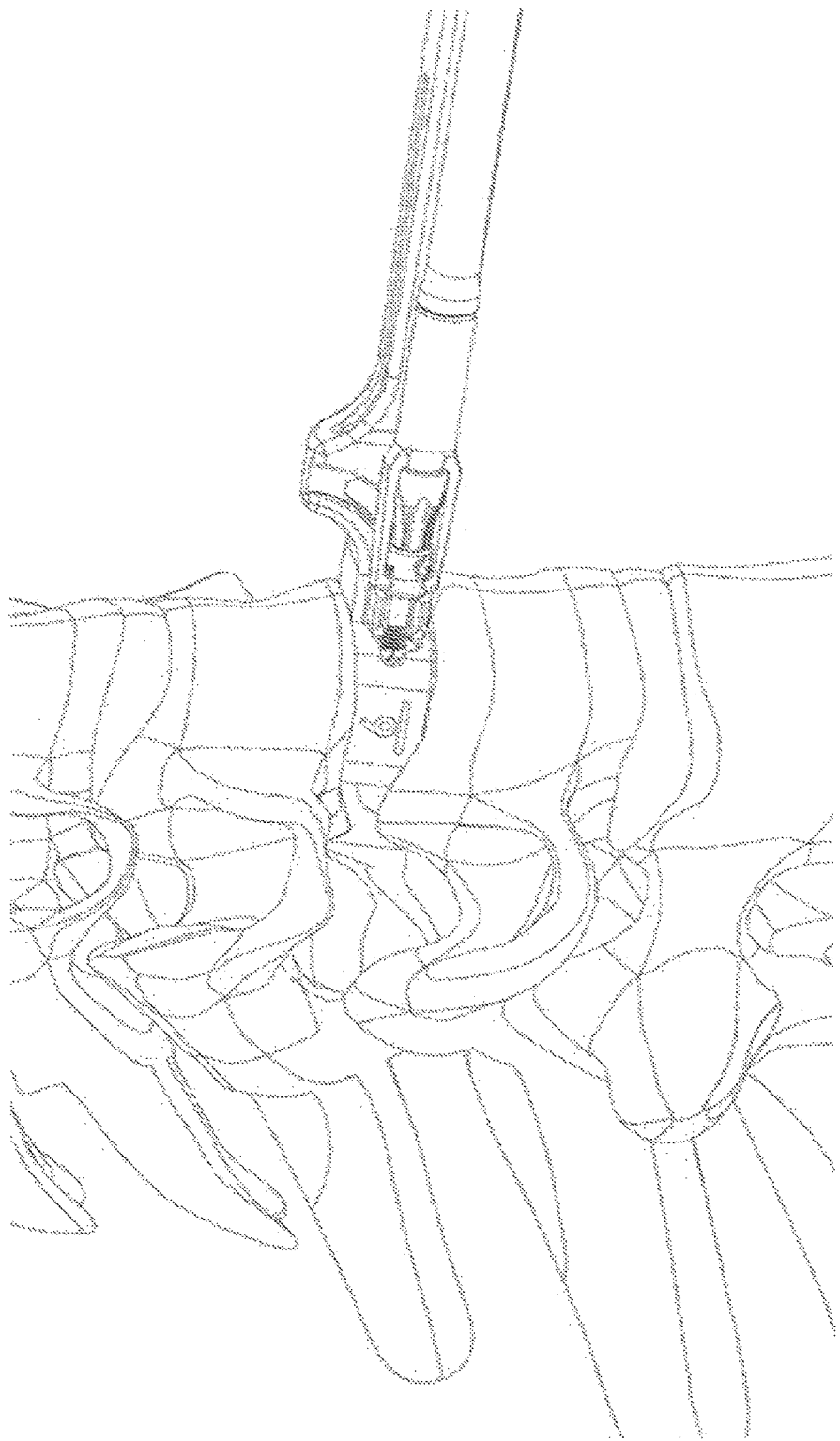
Figure 18:
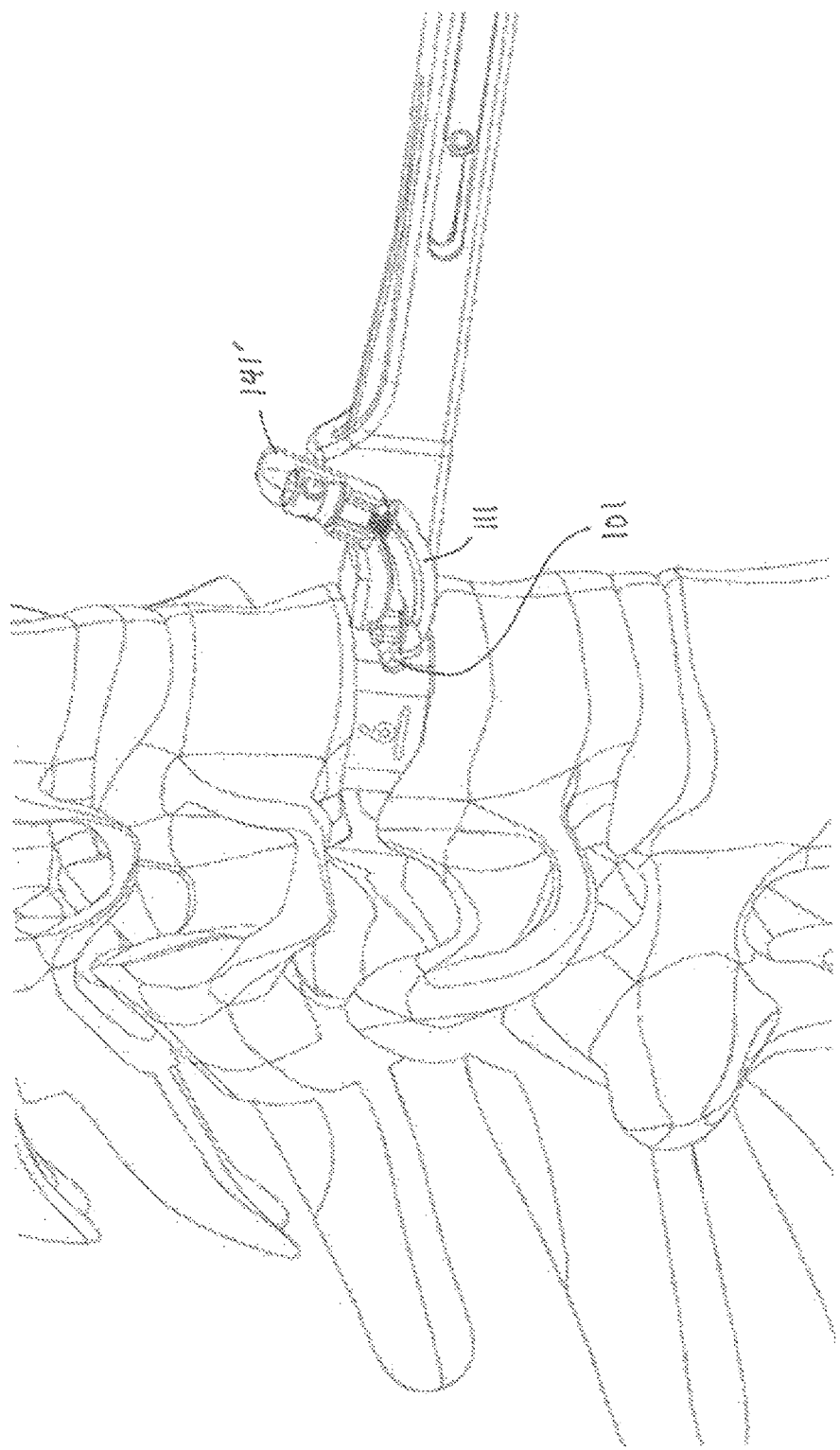

FIGS. 14 to 18 address an embodiment for anchor extraction or withdrawal. FIGS. 14 to 18 show a withdrawal tool 140', the withdrawal tool comprising a first withdrawal tool arm 141' configured to travel along an additional first arcuate path 141" to withdraw the first anchor 111 from the first channel 101. FIGS. 16 and 17 show a threaded rod 145 that threads into the first anchor 111 to couple the anchor to the withdrawal tool arm 141'. In an embodiment anchor 111 is threaded such that a tool (threaded rod 145 of FIG. 16) with, for example, male threads can be threadably coupled to the anchor. The arm 121 is tapered so it is pushed away by rod 145 in a medial direction. In doing so the resilient member 121 no longer retains the anchor in the cage body and the anchor may be removed. Thus, FIGS. 14-18 depict a system for reversing deployment of an anchor in an embodiment of a standalone interbody system. In an embodiment arm 121 is tapered so it is pushed away by articulating arm 141' in a medial direction. Regarding deflection of resilient arms, at times the arms have beveled surfaces and/or the anchors and/or insertion/withdrawal tools have beveled surfaces to deflect resilient arms away from the channel to allow anchor implantation or extraction.

In an embodiment resilient member 120 includes a threaded orifice to couple to a reciprocally threaded insertion tool 143 (FIG. 11). Tool 143 may be rotated via knob 144 (FIG. 7) to couple insertion tool 140 to cage 110. In an embodiment the resilient member 120 comprises a first material, such as Titanium or Nickle Titanium, and the cage (e.g., wall 130) comprises a second material (e.g., Polyether ether ketone (PEEK)) that is softer than the first material. This can be critical for instances such as, for example, when a physician is manipulating cage 110. If the manipulation is particularly forceful the threads being formed in Titanium (instead of something relatively softer such as PEEK) helps resist thread stripping.

In an embodiment (e.g., FIG. 10) the first anchor 111 includes an arcuate outer wall defining an arc 152 that extends along a majority of an overall length of the first anchor. Arc 152 has a single consistent radius of curvature. However, this does not limit all embodiments to anchors with arcs and further other anchors may be primarily linear or have curved surfaces that extend less than a majority of the overall length of the anchors.

In an embodiment (e.g., FIG. 1) the resilient member 120 directly contacts an outer surface of the lateral wall 130 of the cage. This allows a user to visually verify that arms 121, 122 have "snapped back" into position to prevent deployed anchors from 111, 112 from "backing out" of vertebrae and cage 110. However, other embodiments (e.g., FIG. 19) have resilient members that are more interiorly located whereby such visualization may be more limited.

While many examples described herein have shown two channels for two anchors (e.g., FIG. 1), other embodiments are not so limited and may include fewer channels (e.g., 1) or more channels (e.g., 3, 4, or more) for anchors. For example, while a cervical implant may have less "real estate" for such channels a lumbar implant may allow for, as an example, two channels for superior facing anchors and two channels for inferior facing anchors (e.g., FIG. 25).

In an embodiment, orifice 104 (FIG. 1) may go all the way through (FIGS. 5 and 6) member 120 to constitute a channel. Such a channel may allow a physician to inspect channel 103, insert bone matrix or particulate into channel 103, and the like. However, in other embodiments orifice 104 may be sealed at one of its ends.

Embodiments above describe how upon insertion an anchor deforms a resilient member medially (due to, for example, tapered faces of resilient arms and/or tapered faces of the anchors) moving the member out of the channel or void in which it normally resides. After final deployment the resilient member "snaps back" laterally into position. The resilient member now is located at least partially within a void of the anchor (or lateral to the anchor) thereby preventing "backing out" or withdrawal of the anchor. In other words, in some embodiments the resilient member is behind or lateral to the anchor after deployment (e.g., FIG. 1) but in other embodiments the arm may be deployed within a void of the anchor. In some embodiments arms may "snap back" in the same direction. For example, in an embodiment resilient arms may both be located to the left of channels and may both deflect to the left to allow anchor passage and "snap back" to the right. In some embodiments more than one arm may obstruct a portion of a channel.

In an embodiment the anchors include a guide on a side wall that mates with a channel in the cage (or vice versa in some embodiments). Anchors may include teeth or other gripping members to grip bone or tissue upon implantation. The cage body (which may include PEEK) may include apertures that retain radiopaque metal members (see, e.g., 146 of FIG. 5) to allow for imaging of such metal members. For example, Tantalum pins 146 may be used to aid visualization of image transparent PEEK body 110. In an embodiment portions of the body 110 may be coated with a material, such as titanium to promote tissue ingrowth.

The main cage body may have ramps or angled portions (see, e.g., element 153 of FIG. 10) that help project anchors in superior and inferior directions respectively to deploy into bone portions located superior and inferior to the spacer. In an embodiment the anchors are curved (see FIG. 10). The curved nature of the anchors allows for a more vertical implantation into bone. For example, a flattened anchor portion 154 is generally vertical in FIG. 10 illustrating an insertion path that generally has more than 45 degrees of rotation. For example, from insertion (FIG. 8) to final implantation (FIG. 10) the tip of the anchor may rotate 45, 55, 65, 75, 85 degrees or more. This results in better purchase with the vertebrae. For example, in FIG. 8 the distal tip of anchor 111 is generally horizontal and in FIG. 10 is generally vertical constituting almost a 90 degree rotation. This eases implantation for the physician while still provide for secure bone purchase.

FIGS. 7-13 depict an insertion tool for the anchors. The insertion tool allows for simultaneous insertion of anchors into bone. The anchors 111, 112 may deploy simultaneously in superior and inferior directions. By "simultaneous" what is meant is that at some point in time both anchors are being deployed (e.g., FIG. 12). Simultaneous does not necessarily require that each anchor move in lock step with each other (e.g., FIG. 11 shows one anchor further progressed than the other anchor) but in some embodiments that is indeed the case. However, in other embodiments the anchors may be deployed independently/non-simultaneously of each other (e.g., one deployed and then another deployed). For example, the same tool shown in FIG. 7 may be deployed with only a single anchor and is so doing only a single anchor is deployed regardless of arms 141, 142 both articulating simultaneously. Another embodiment of tool 140 may include only a single arm that still advances along an arcuate path to project a single anchor along a superior or inferior arcuate path.

As shown in FIG. 2, one anchor projects upwards and another anchor projects downwards. The anchors are not vertically aligned but are present in the same horizontal plane (e.g., a plane that intersects both channels), a plane that aligns with the main axis of the spacer. The anchors are equally offset from the vertical axis (e.g., a vertical axis that bisects the orifice of element 120). Due to this offset, multiple instances of the body may be employed in a multi-level fusion. In such a case, a first body may be inserted into disc space above a vertebra and a second body may be inserted into disc space below that same vertebra. Due to the offset of the anchors, even if the bodies are aligned vertically, the upward projecting anchor of the lower second body will not interfere with a downward projecting anchor of the upper first body. Embodiments include a set of multiple cages for a multilevel fusion as described above. Further, due to the offset between anchors each of the anchor channels may traverse more than 50% of the height of the body (e.g., start in the bottom half of the cage and traverse through the top half of the cage). If the body is configured for cervical fusion, the body is necessarily quite small (e.g., as opposed to lumbar bodies) and therefore "real estate" is limited. However, staggering of the anchors allows for longer and thicker anchors that have greater strength to accommodate both insertion but also post-operative loading.

An embodiment includes a set of anchors that come in varying lengths, any of which are compatible with either of the body channels simply by rotating the nail 180 degrees if switching between deployment in channels. Having an assortment of anchors to choose from allows a physician to use an anchor pair for a single body whereby the anchors are equal or unequal lengths. In an embodiment a physician may insert a relatively smaller anchor using the technique of FIGS. 7-13, then explant the smaller anchor using the technique of FIGS. 14-18, and then insert a relatively larger anchor using the technique of FIGS. 7-13.

Embodiments are not limited to any one type of a spacer and may be used for cervical, thoracic, and lumbar spacers.

Figure 19:
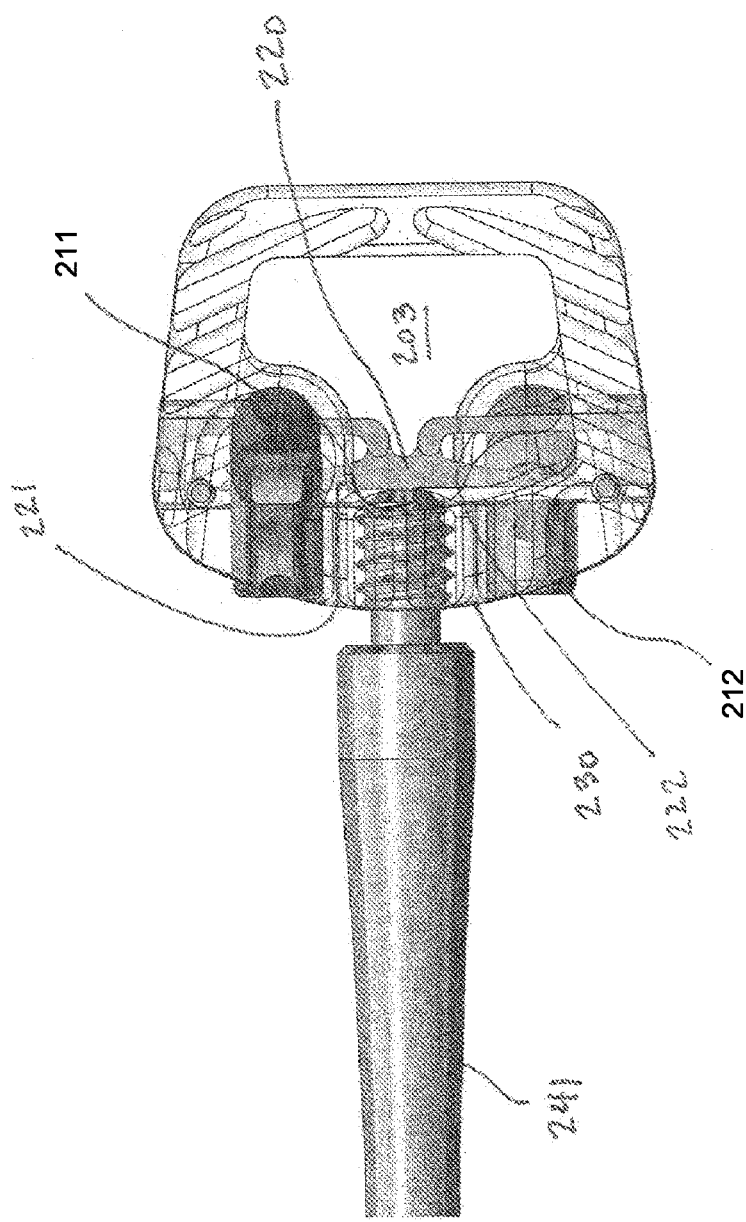
FIGS. 19, 20, and 21 include cross-sectional views of an embodiment of a standalone interbody cage and anchors.
Figure 20:
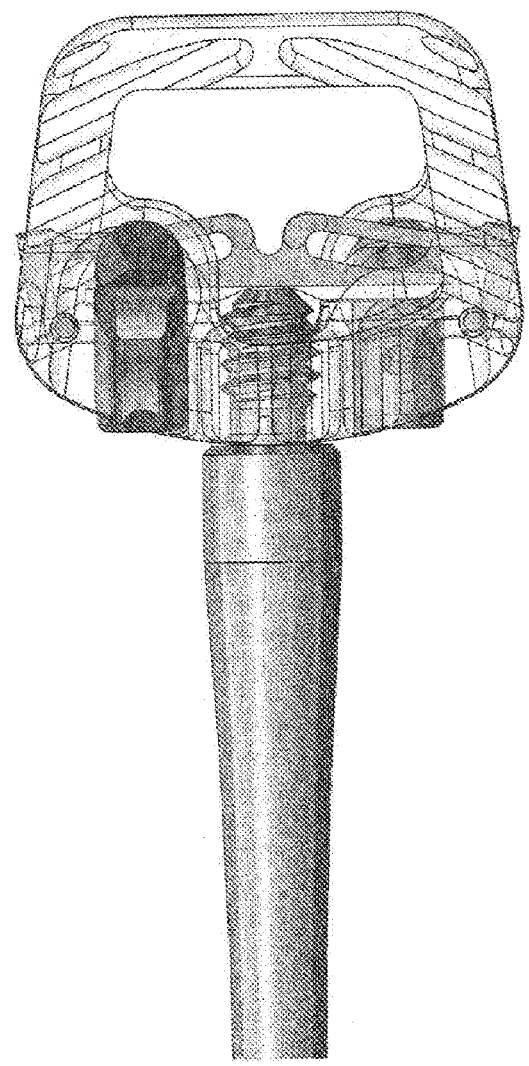
Figure 21:
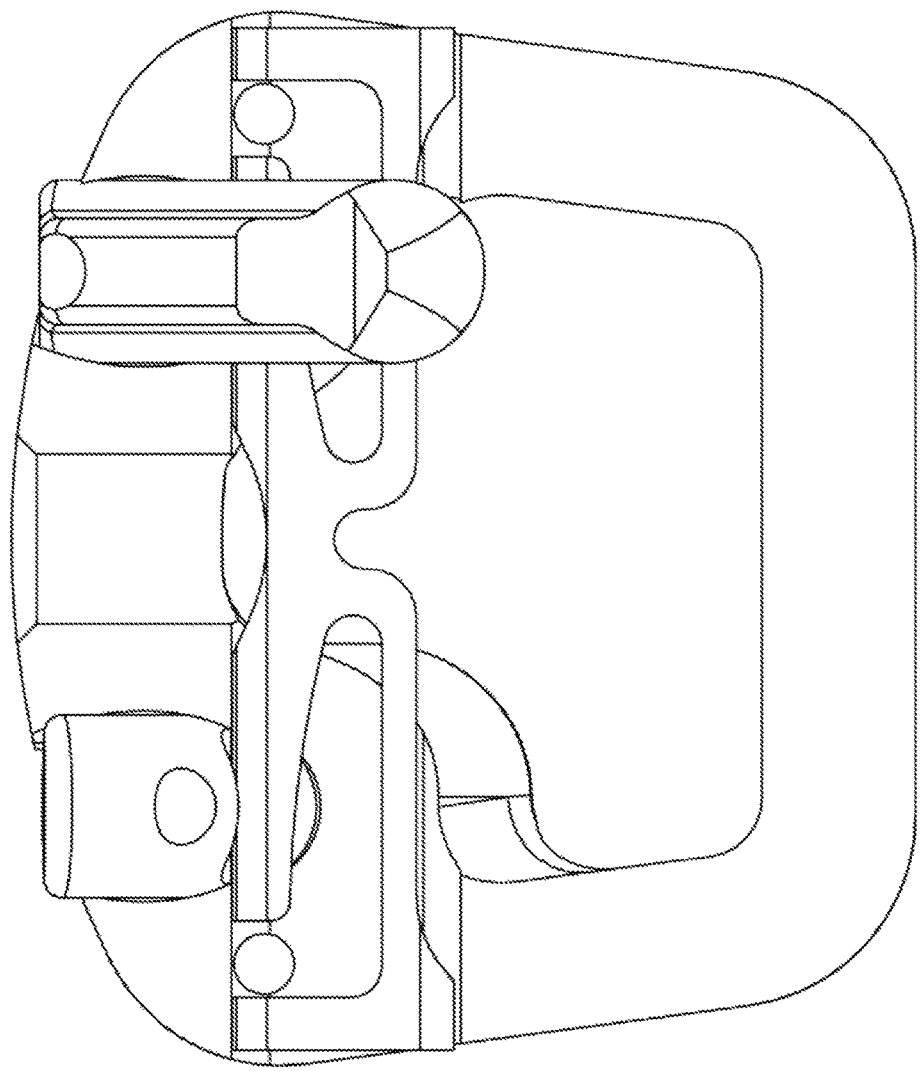

FIGS. 19, 20, 21 include an orthopedic fusion system comprising: a cage; a curved first channel (occupied by anchor 211) coupling a lateral wall 230 of the cage to a superior surface of the cage; a curved second channel (occupied by anchor 212) coupling the lateral wall of the cage to an inferior surface of the cage; a third channel 203 coupling the superior surface of the cage to the inferior surface of the cage; a curved first anchor 211 configured to slide within the first channel; a curved second anchor 212 configured to slide within the second channel; and a resilient member 220 comprising a resilient first arm 221 that projects across a portion of the first channel and a resilient second arm 222 that projects across a portion of the second channel.

In such an embodiment an insertion tool may include an arm 241 that couples to the cage to force the resilient member towards channel 203 (FIG. 20) thereby flexing arms 221, 222 to move away from the channels. Those arms may later "snap back" behind the anchors or into recesses in the anchors to keep the anchors from "backing out" of the bone. For withdrawal of anchors the arm 241 may again be deployed to move the arms out of a restricting position and then hooks or other members may be used to withdraw the anchors. FIG. 21 shows the resilient member in an unflexed state with resilient arms abutting walls of anchors to prevent anchor "back out".

Figure 22:
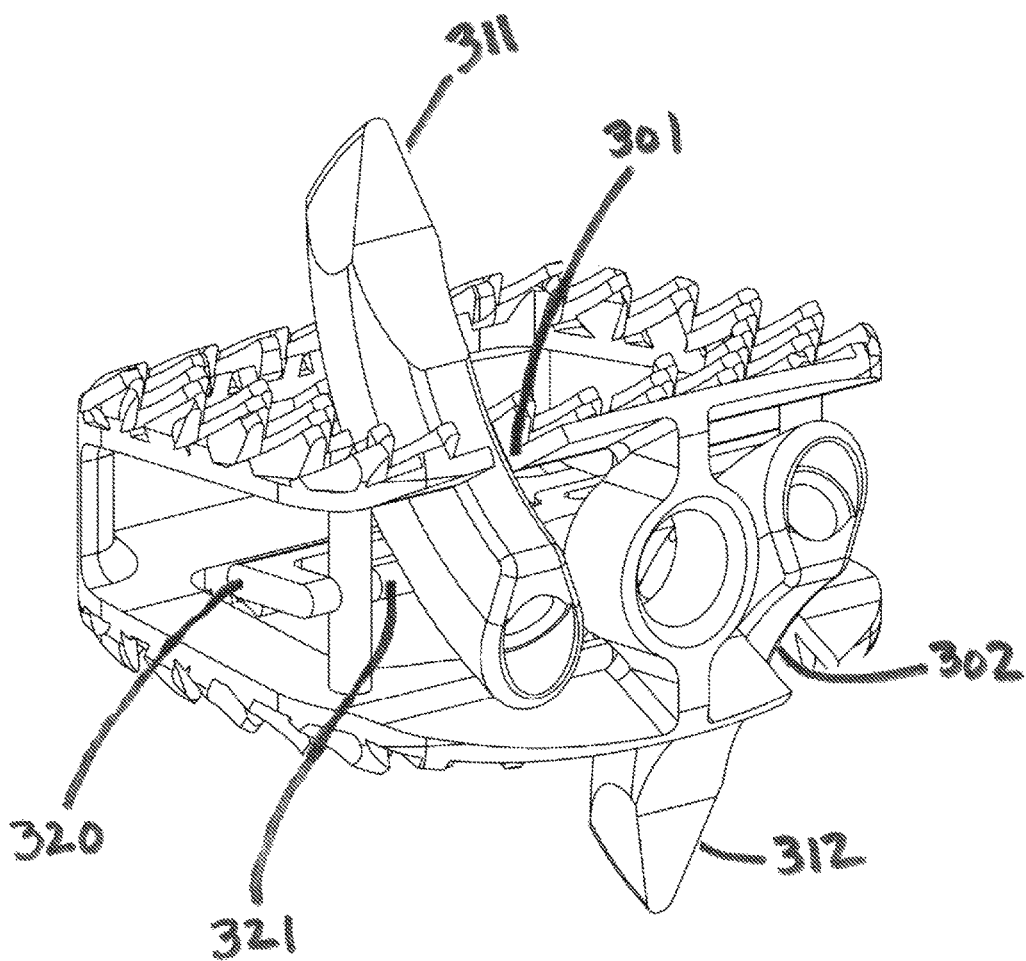
FIGS. 22, 23, 24 include perspective views of an embodiment of a standalone interbody cage and anchors.
Figure 23:
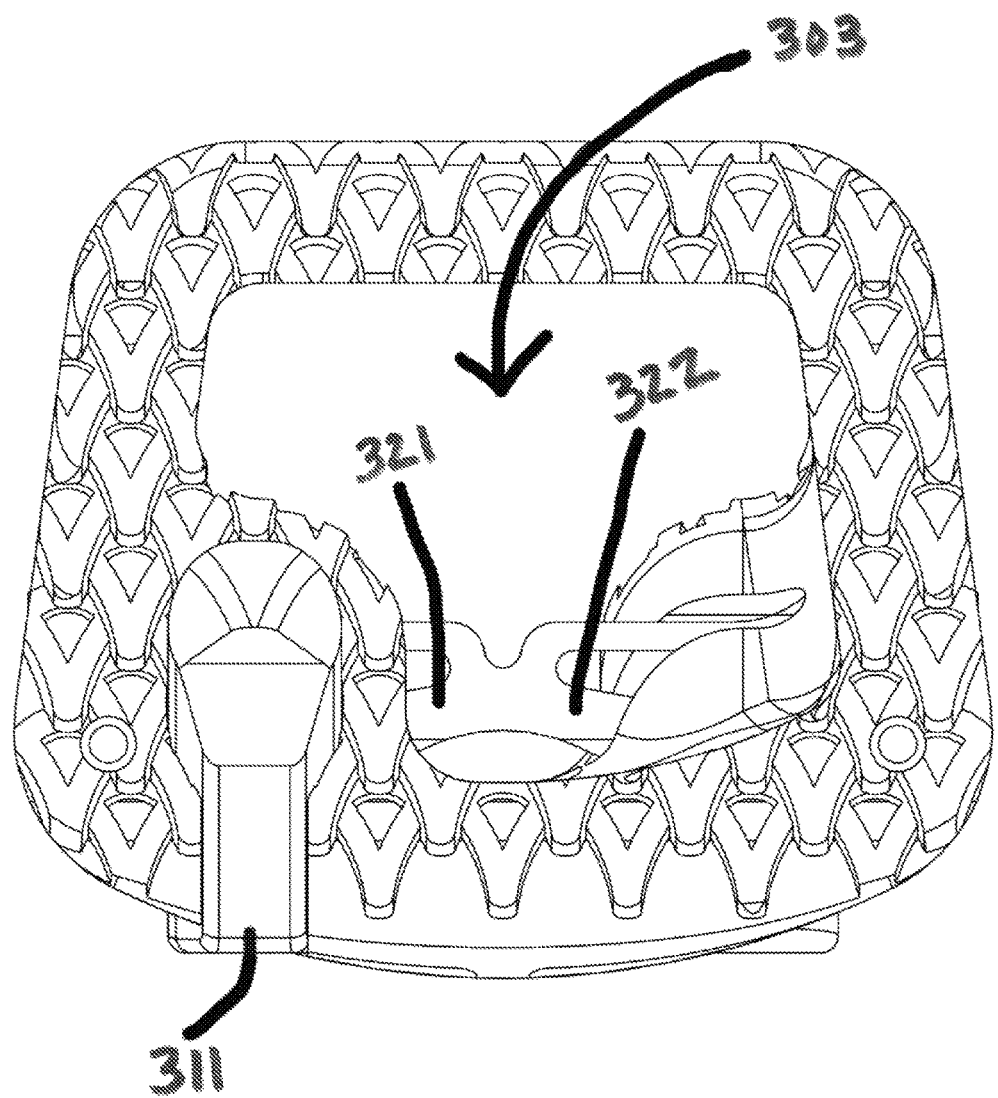
Figure 24:
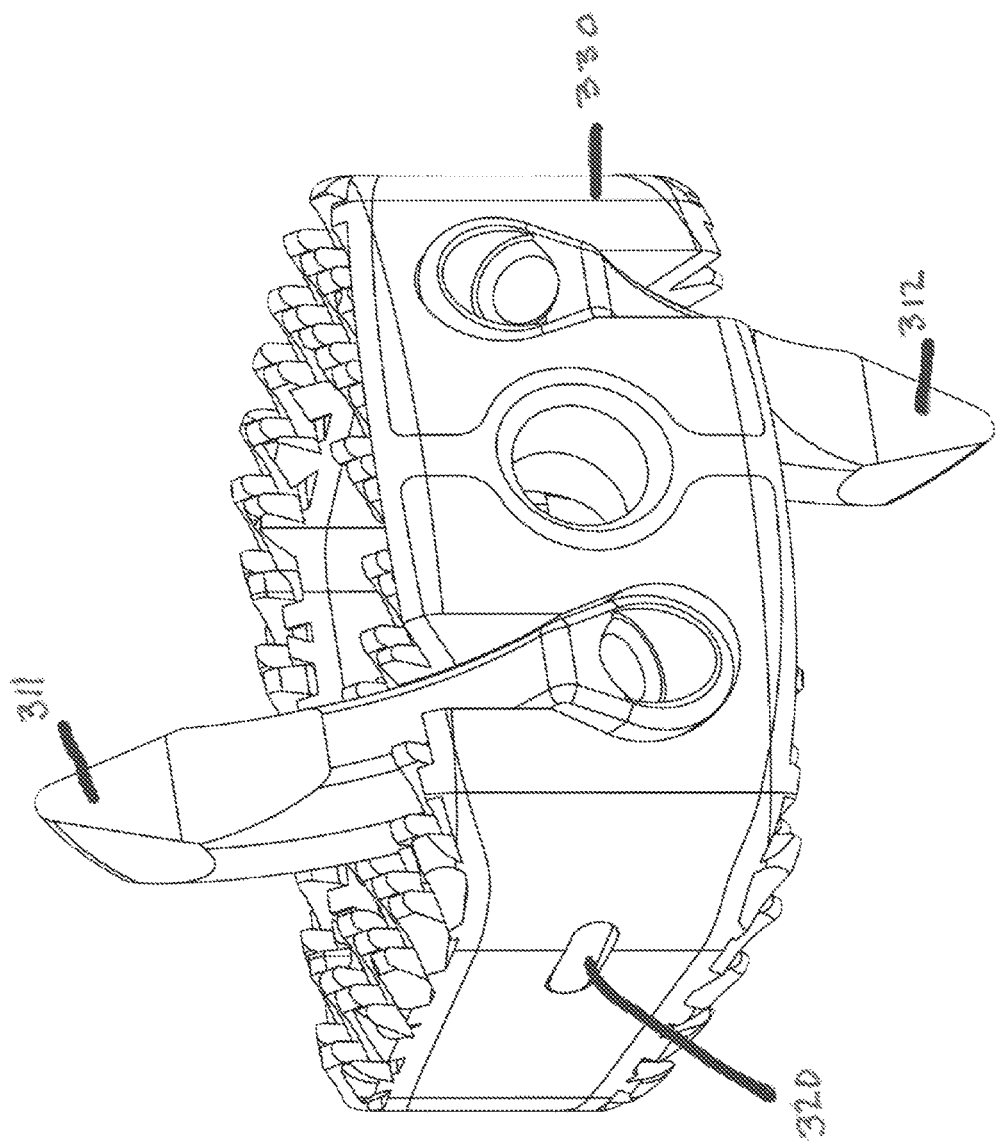

FIGS. 22, 23, 24 include perspective views of an embodiment of a standalone interbody cage and anchors. FIG. 22 shows a Titanium skeleton formed using, for example, additive manufacturing. FIGS. 23, 24 show the skeleton filled out with PEEK (e.g., after PEEK is injection molded into the cage). FIGS. 23, 24 include an orthopedic fusion system comprising: a cage; a curved first channel 301 (occupied by anchor 311) (e.g., where channel may be milled within PEEK) coupling a lateral wall 330 of the cage to a superior surface of the cage; a curved second channel 302 (occupied by anchor 312) coupling the lateral wall of the cage to an inferior surface of the cage; a third channel 303 coupling the superior surface of the cage to the inferior surface of the cage; a curved first anchor 311 configured to slide within the first channel; a curved second anchor 312 configured to slide within the second channel; and a resilient member 320 comprising a resilient first arm 321 that projects across a portion of the first channel and a resilient second arm 322 that projects across a portion of the second channel.

In such an embodiment an insertion tool may include an arm that couples to the cage to force the resilient member towards channel 303 thereby flexing arms 321, 322 to move away from the channels. Those arms may later "snap back" behind the anchors or into recesses in the anchors to keep the anchors from "backing out" of the bone. For withdrawal of anchors the arm may again be deployed to move the arms out of a restricting position and then hooks or other members may be used to withdraw the anchors.

Figure 25:
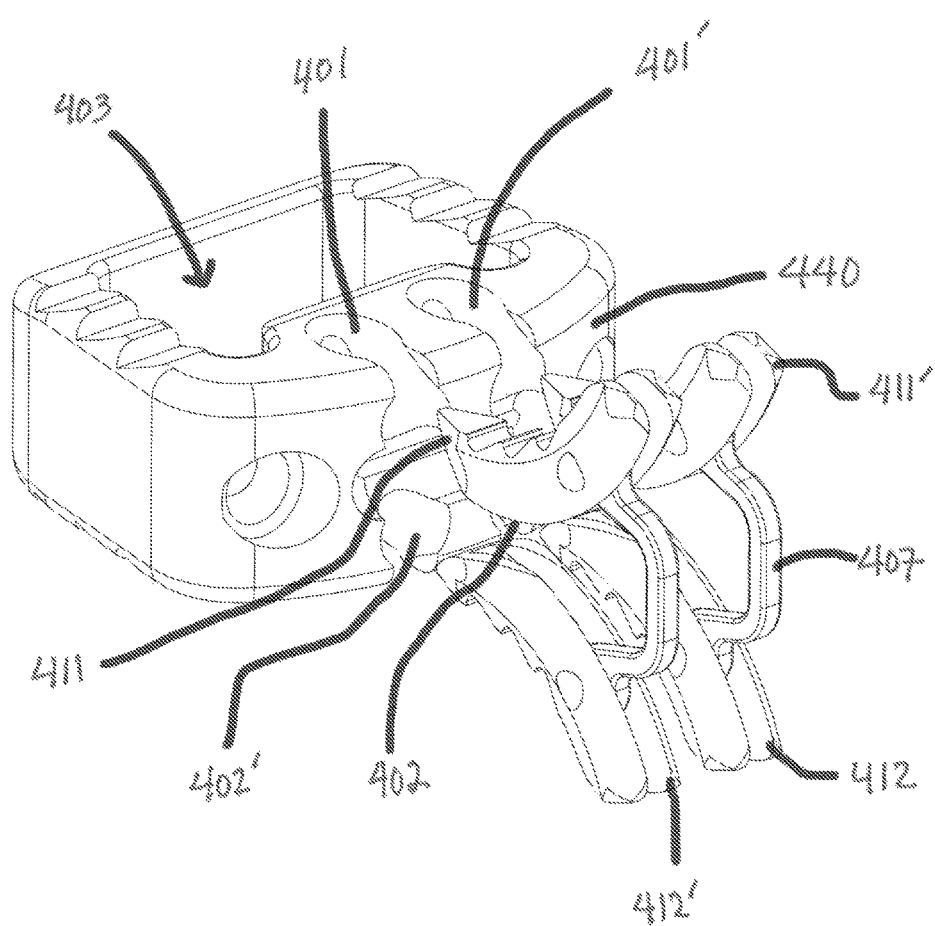
FIG. 25 includes a perspective view of an embodiment of a standalone interbody cage and anchors.

FIG. 25 includes a perspective view of an embodiment of a standalone interbody cage and anchors. FIG. 25 includes an orthopedic fusion system comprising: a cage; curved channels 401, 401' coupling a lateral wall 440 of the cage to a superior surface of the cage; curved channels 402, 402' coupling the lateral wall of the cage to an inferior surface of the cage; a channel 403 coupling the superior surface of the cage to the inferior surface of the cage; curved anchors 411, 411' configured to slide within the channels 401, 401'; curved anchors 412, 412' configured to slide within the channels 402, 402'. No resilient member analogous to member 320 (FIG. 22) is present as not all embodiments require such a member. Member 407 (which couples anchors to each other in a pivotal manner where anchors pivot about member 407) may be resilient and include, for example, nickel titanium.

Figure 26:
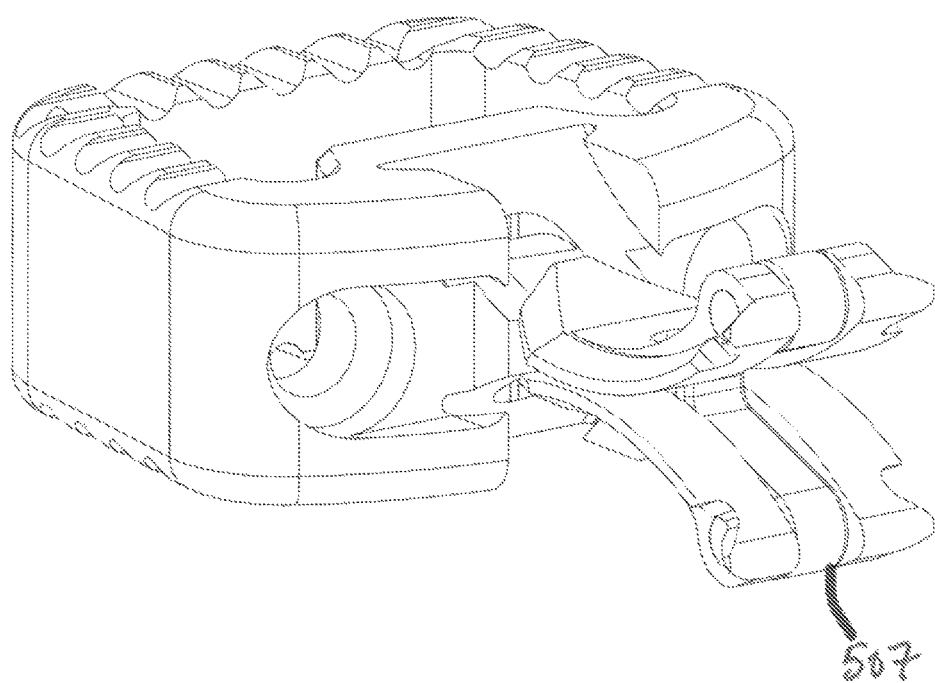
FIG. 26 includes a perspective view of an embodiment of a standalone interbody cage and anchors.

While many of the anchors shown thus far resemble nails and may have cross-sections that are generally cylindrical other embodiments may have more flattened anchors and the like. For example, FIG. 26 shows two flattened anchors that deploy simultaneously. In this embodiment the anchors are pivotally coupled to one another via resilient member 507 but they need not be in order to still simultaneously deploy. FIG. 26 shows two flattened channels configured to receive the flattened anchors. Anchors may have multiple tines (not shown) that share a common base and the like. Flattened anchors may be deployed offset from each other whereby flattened anchors are deployed in channels offset from each other (such as with FIG. 1).

The designs of various resilient members described herein are such that they may be deformed yet still maintain mechanical integrity after cycling or repeated deformation of the members (which may be brought on due to insertion of the member in the device and a physician inserting anchors and then removing those anchors to later deploy additional anchors (possibly of a smaller or larger size than the initially deployed anchors)).

Figure 28:
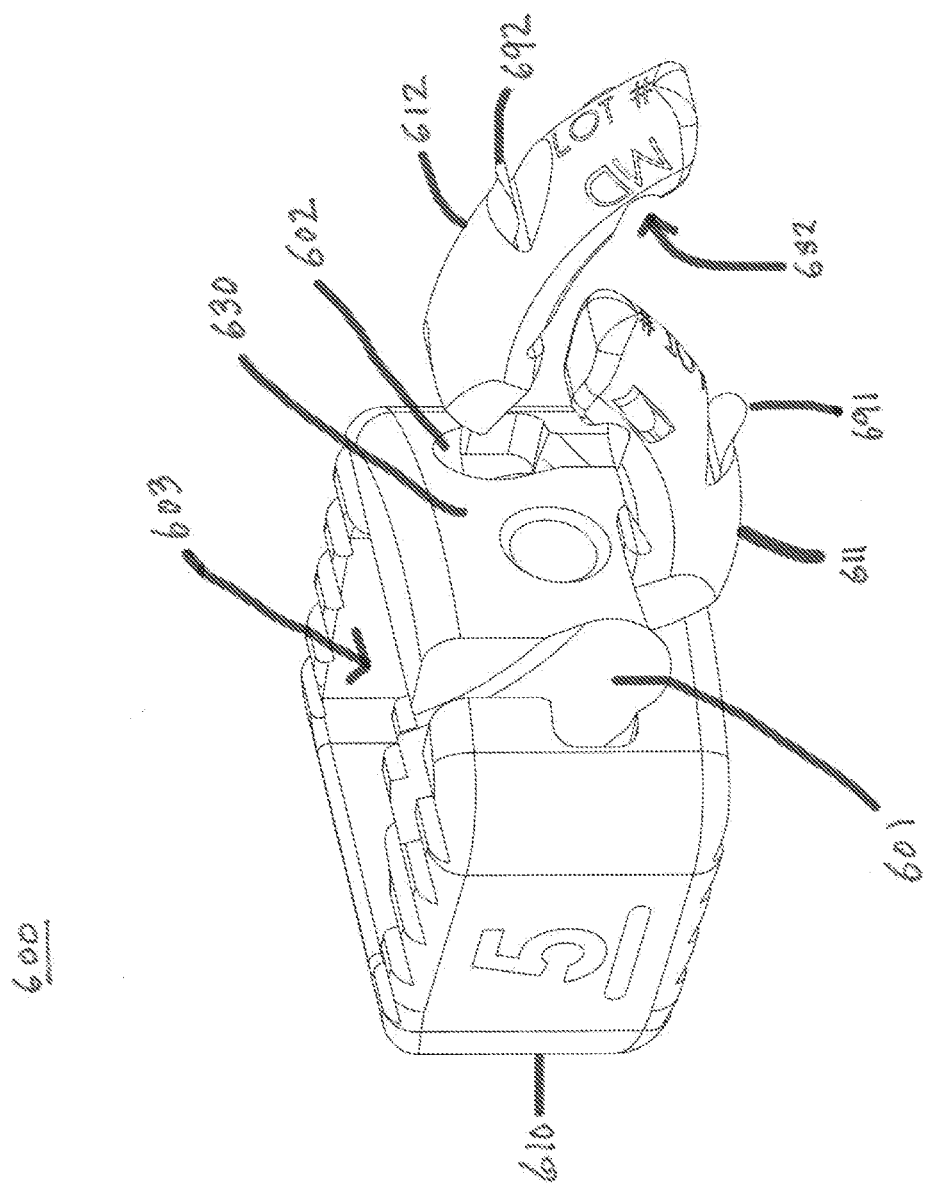
FIGS. 28, 29, 30 include various views of an embodiment of a standalone interbody cage and anchors.
Figure 29:
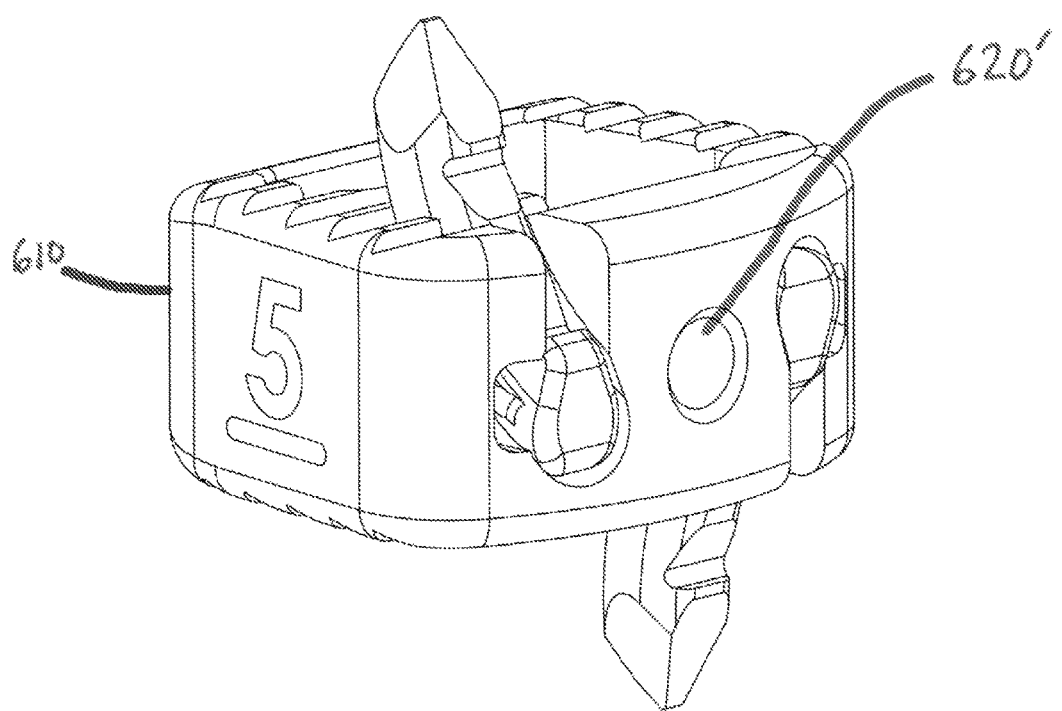
Figure 30:
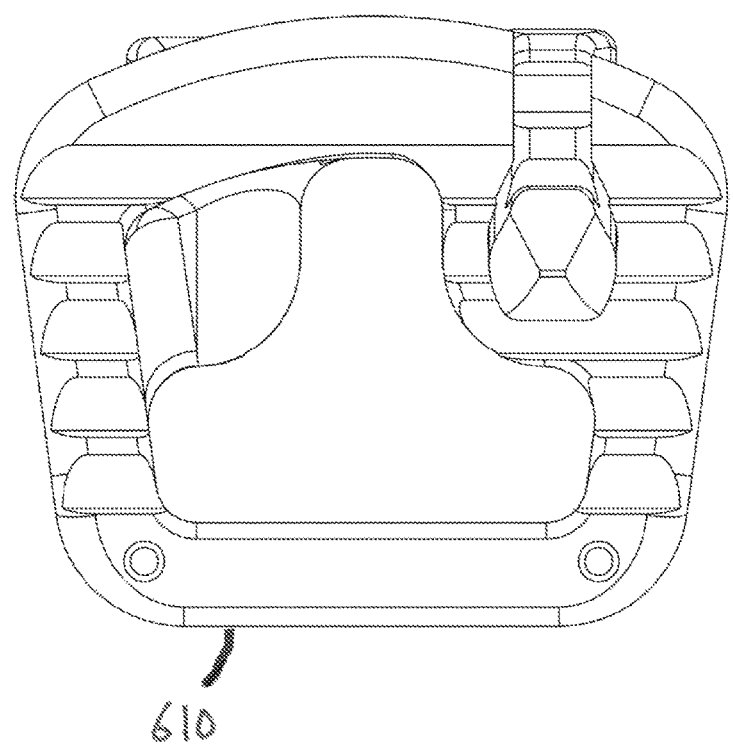

FIGS. 28, 29, 30 include an orthopedic fusion system 600 comprising: a cage 610; a curved first channel 601 coupling a lateral wall 630 of the cage to a superior surface of the cage; a curved second channel 602 coupling the lateral wall of the cage to an inferior surface of the cage; a third channel 603 coupling the superior surface of the cage to the inferior surface of the cage; a curved first anchor 611 configured to slide within the first channel; a curved second anchor 612 configured to slide within the second channel. Instead of a resilient member analogous to member 120 of FIG. 1, the embodiment of system 600 comprises barbs 691, 692 to wedge within portions of the material (e.g., PEEK) that forms channels 601, 602. Thus, resilient retention arms are not necessary in all embodiments. However, the embodiment of system 600 may be augmented with resilient arms. An anchor may be removed by coupling a hook member to recess 682 and then pulling the anchor out of the cage. An insertion tool may couple to orifice 620' to deploy or extract the cage. Orifice 620' may be threaded to receive the insertion tool. The threads may be composed from PEEK, a metal liner, and the like.

The following examples pertain to further embodiments.

Example 1 includes an orthopedic fusion system comprising: a cage; a curved first channel coupling a lateral wall of the cage to a superior surface of the cage; a curved second channel coupling the lateral wall of the cage to an inferior surface of the cage; a third channel coupling the superior surface of the cage to the inferior surface of the cage; a curved first anchor configured to slide within the first channel; a curved second anchor configured to slide within the second channel; and a resilient member comprising a resilient first arm that projects across a portion of the first channel and a resilient second arm that projects across a portion of the second channel.

The "superior surface" does not necessarily mean it must be the "most" superior surface or highest surface of the cage. The "inferior surface" does not necessarily mean it must be the "most" inferior surface or lowest surface of the cage.

The portion of the channel that the arms project across may be, for example, at a proximal portion of the channel or distal to the proximal end of the channel (where proximal end is where the anchor initially inserts into the channel).

The lateral wall need not be completely flat. For example, the wall may include a ridge within but still constitute a single lateral wall. As used herein lateral wall does not necessarily mean lateral with regard to the patient but more generally means a side wall. The wall may face, for example, anterior or posterior when inserted into a patient.

Example 2 includes the system of example 1 wherein the first and second arms are monolithic with one another.

Other embodiments may employ multiple resilient arms that are not monolithic with each other.

Example 3 includes the system of example 1 wherein in a first orientation the first anchor directly deflects the first arm away from the first channel to allow the first anchor to pass within the first channel.

This deflection may be aided by beveled surfaces on the arms, anchors, and/or insertion tools.

Example 4 includes the system of example 3 wherein in the first orientation the second anchor directly deflects the second arm away from the second channel to allow the second anchor to pass within the second channel.

Example 5 includes the system of example 3 wherein in a second orientation: (a) a portion of the first arm is lateral to a proximal end of the first anchor and prevents the first anchor from backing out of the first channel, and (b) the first anchor does not deflect the first arm away from the first channel.

Example 6 includes the system of example 5, wherein in a vertical plane in the second orientation the first anchor is completely surrounded by an interior wall of the first channel.

For example, see FIGS. 4 and 10 showing how in a vertical plane the anchor is surrounded in 360 degrees by interior wall of the channel. This is in contrast to, for example, FIG. 28 where a slot joins the channel to prevent 360 degrees of surrounding wall in a vertical plane.

Example 7 includes the system of example 1 wherein the first anchor includes a projection configured to abut a wall of the first channel to prevent a proximal portion of the first anchor from passing through the first channel.

Examples of such projections include element 111' (FIG. 1) and 692 (FIG. 28). Other embodiments may use recesses in the anchors that couple to resilient members of the cage to stop progress of the anchor.

Example 8 includes the system of example 1 comprising an insertion tool, the insertion tool comprising: a first insertion tool arm configured to travel along a first arcuate path to drive the first anchor along the first channel; a second insertion tool arm configured to travel along a second arcuate path to drive the second anchor along the second channel.

An arcuate path need not maintain a single radius of curvature along its entire path but may indeed include such a single radius of curvature in some embodiments.

Example 9 includes the system of example 8 wherein the first and second insertion tool arms are configured to respectively travel along the first and second arcuate paths simultaneously with one another.

Example 10 includes the system of example 8 comprising a withdrawal tool, the withdrawal tool comprising a first withdrawal tool arm configured to travel along an additional first arcuate path to withdraw the first anchor from the first channel.

Example 11 includes the system of example comprising a fourth channel coupling the lateral wall of the cage to the third channel.

Example 12 includes the system of example 1 comprising: a fourth channel between the first and second channels; a third anchor configured to slide within the fourth channel.

Example 13 includes the system of example 1 wherein a horizontal axis intersects the lateral wall and the first and second channels.

Example 14 includes the system of example 1 wherein the first anchor includes an arcuate outer wall defining an arc that extends along a majority of an overall length of the first anchor.

Example 15 includes the system of example 14 wherein the arc has a single consistent radius of curvature.

Example 16 includes the system of example 1 wherein in a first orientation the first anchor directly deflects the first arm towards the second arm and away from the first channel to allow the first anchor to pass within the first channel.

Example 17 includes the system of example 1 wherein: the resilient member comprises a first material; the cage comprises a second material that is softer than the first material; and the resilient member directly contacts an outer surface of the lateral wall of the cage.

Example 18 includes the system of example 17 wherein: the first anchor includes a threaded orifice to couple to a reciprocally threaded withdrawal tool; and the resilient member includes an additional threaded orifice to couple to a reciprocally threaded insertion tool.

Example 19 includes the system of example 1 wherein the first and second anchors are configured to deploy into the first and second channels simultaneously with one another.

Example 20 includes an orthopedic fusion system comprising: a cage; a first channel coupled to a lateral wall of the cage and projecting superiorly; a second channel coupled to the lateral wall of the cage and projecting inferiorly; a third channel coupling a superior surface of the cage to an inferior surface of the cage; a curved first anchor configured to slide within the first channel; a curved second anchor configured to slide within the second channel; and a resilient member comprising a resilient first arm that projects across a portion of the first channel and a resilient second arm that projects across a portion of the second channel.

Example 21 includes the system of example 20 wherein a horizontal axis intersects the lateral wall, the resilient member, and the first and second channels.

Example 22 includes the system of example 20 comprising an insertion tool, the insertion tool comprising: a first insertion tool arm configured to travel along a first path to drive the first anchor along the first channel; a second insertion tool arm configured to travel along a second path to drive the second anchor along the second channel.

Example 23 includes the system of example 8 wherein the insertion tool comprises a third insertion tool arm configured to drive the resilient member towards the channel (103).

Example 24 includes the system of example 23 wherein the third insertion tool arm is configured to drive the first and second arms towards each other in response to the third insertion tool arm driving the resilient member towards the third channel.

Example 25 includes the system of example 3 wherein in the first orientation the second anchor is not included in the second channel.

Example 26 includes the system of example 1 wherein the first and second anchors are configured to deploy into the first and second channels asynchronously from one another.

Example 27 includes the system of example 8 comprising a withdrawal tool, the withdrawal tool comprising: a first withdrawal tool arm configured to travel along an additional first arcuate path to withdraw the first anchor from the first channel; a second withdrawal tool arm configured to travel along an additional second arcuate path to withdraw the second anchor from the second channel.

Example 28 includes the system of example 1 wherein the first anchor includes a retention member configured to prevent a proximal portion of the first anchor from passing through the first channel.

Example 29 includes the system of example 1 wherein the first and second anchors are pivotally coupled to one another.

Example 30 includes an orthopedic fusion system comprising: a cage; a curved first channel coupling a lateral wall of the cage to a superior surface of the cage; a curved second channel coupling the lateral wall of the cage to an inferior surface of the cage; a third channel coupling the superior surface of the cage to the inferior surface of the cage; a curved first anchor configured to slide within the first channel; a curved second anchor configured to slide within the second channel.

Thus, not all embodiments require a resilient member.

Example 31 includes the system of example 30 wherein the cage includes a vertical plane that bisects the cage into left and right halves and the first channel is included one of the left and right halves and the second channel is included in another of the left and right halves.

Example 32 includes an orthopedic fusion system comprising: a cage; a first channel coupling a lateral wall of the cage to a superior surface of the cage; a second channel coupling the lateral wall of the cage to an inferior surface of the cage; a third channel coupling the superior surface of the cage to the inferior surface of the cage; a first anchor configured to slide within the first channel; a second anchor configured to slide within the second channel; and a resilient member comprising a resilient first arm that projects across a portion of the first channel and a resilient second arm that projects across a portion of the second channel.

Thus, not all embodiments require curved channels and/or curved anchors.

Example 33 includes the system of example 32 wherein in a first orientation the first anchor directly deflects the first arm away from the first channel to allow the first anchor to pass within the first channel.

Example 34 includes the system of example 33 wherein in the first orientation the second anchor directly deflects the second arm away from the second channel to allow the second anchor to pass within the second channel.

Example 35 includes the system of example 32 wherein the first and second anchors are configured to deploy into the first and second channels simultaneously with one another.

Example 36 includes the system of example 32 wherein the cage includes a vertical plane that bisects the cage into left and right halves and the first channel is included one of the left and right halves and the second channel is included in another of the left and right halves.

Example 37 includes an orthopedic fusion system comprising: a cage; a curved first channel coupling at least one side wall of the cage to a superior surface of the cage; a curved second channel coupling the at least one side wall of the cage to an inferior surface of the cage; a third channel coupling the superior surface of the cage to the inferior surface of the cage; a curved first anchor configured to slide within the first channel; a curved second anchor configured to slide within the second channel; and a resilient member comprising a resilient first arm that projects across a portion of the first channel and a resilient second arm that projects across a portion of the second channel.

Thus, in an embodiment the channels are not necessarily in the same side wall but may be included in two adjoining wall.

Embodiments are not limited to any one approach (anterior, posterior, lateral).

An embodiment includes a kit with a cage and several anchors that have the same width but different lengths.

The foregoing description of the embodiments of the invention has been presented for the purposes of illustration and description. It is not intended to be exhaustive or to limit the invention to the precise forms disclosed. This description may include terms, such as left, right, top, bottom, over, under, upper, lower, first, second, etc. that are used for descriptive purposes only and are not to be construed as limiting. For example, terms designating relative vertical position refer to a situation where a side of a device is the "top" surface of that device; however the device may actually be in any orientation so that a "top" side of a device may be lower than the "bottom" side in a standard terrestrial frame of reference and still fall within the meaning of the term "top." Persons skilled in the art will recognize various equivalent combinations and substitutions for various components shown in the Figures. It is therefore intended that the scope of the invention be limited not by this detailed description.

What is claimed is:

1. An orthopedic fusion system comprising:
   a cage;
   a curved first channel coupling a lateral wall of the cage to a superior surface of the cage;
   a curved second channel coupling the lateral wall of the cage to an inferior surface of the cage;
   a third channel coupling the superior surface of the cage to the inferior surface of the cage;
   a curved first anchor configured to slide within the first channel;
   a curved second anchor configured to slide within the second channel; and
   a resilient member comprising a resilient first arm that projects across a portion of the first channel and a resilient second arm that projects across a portion of the second channel;
   wherein in a first orientation the first anchor directly deflects the first arm away from the first channel to allow the first anchor to pass within the first channel.

2. The system of claim 1 wherein the first and second arms are monolithic with one another.

3. The system of claim 1 wherein in the first orientation the second anchor directly deflects the second arm away from the second channel to allow the second anchor to pass within the second channel.

4. The system of claim 1 wherein in a second orientation: (a) a portion of the first arm is lateral to a proximal end of the first anchor and prevents the first anchor from backing out of the first channel, and (b) the first anchor does not deflect the first arm away from the first channel.

5. The system of claim 4, wherein in a vertical plane in the second orientation the first anchor is completely surrounded by an interior wall of the first channel.

6. The system of claim 1 wherein the first anchor includes a projection configured to abut a wall of the first channel to prevent a proximal portion of the first anchor from passing through the first channel.

7. The system of claim 1 comprising an insertion tool, the insertion tool comprising:
   a first insertion tool arm configured to travel along a first arcuate path to drive the first anchor along the first channel;
   a second insertion tool arm configured to travel along a second arcuate path to drive the second anchor along the second channel.

8. The system of claim 7 wherein the first and second insertion tool arms are configured to respectively travel along the first and second arcuate paths simultaneously with one another.

9. The system of claim 7 comprising a withdrawal tool, the withdrawal tool comprising
   a first withdrawal tool arm configured to travel along an additional first arcuate path to withdraw the first anchor from the first channel.

10. The system of claim 1 comprising a fourth channel coupling the lateral wall of the cage to the third channel.

11. The system of claim 1 comprising:
    a fourth channel between the first and second channels;
    a third anchor configured to slide within the fourth channel.

12. The system of claim 1 wherein a horizontal axis intersects the lateral wall and the first and second channels.

13. The system of claim 1 wherein the first anchor includes an arcuate outer wall defining an arc that extends along a majority of an overall length of the first anchor.

14. The system of claim 13 wherein the arc has a single consistent radius of curvature.

15. The system of claim 1 wherein in the first orientation the first anchor directly deflects the first arm towards the second arm and away from the first channel to allow the first anchor to pass within the first channel.

16. The system of claim 1 wherein:
the resilient member comprises a first material;
the cage comprises a second material that is softer than the first material; and
the resilient member directly contacts an outer surface of the lateral wall of the cage.

17. The system of claim 16 wherein:
the first anchor includes a threaded orifice to couple to a reciprocally threaded withdrawal tool; and
the resilient member includes an additional threaded orifice to couple to a reciprocally threaded insertion tool.

18. The system of claim 1 wherein the first and second anchors are configured to deploy into the first and second channels simultaneously with one another.

19. An orthopedic fusion system comprising:
a cage;
a first channel coupled to a lateral wall of the cage and projecting superiorly;
a second channel coupled to the lateral wall of the cage and projecting inferiorly;
a third channel coupling a superior surface of the cage to an inferior surface of the cage;
a curved first anchor configured to slide within the first channel;
a curved second anchor configured to slide within the second channel;
a resilient member comprising a resilient first arm that projects across a portion of the first channel and a resilient second arm that projects across a portion of the second channel; and
an insertion tool comprising: (a) a first insertion tool arm configured to travel along a first arcuate path to drive the first anchor along the first channel, (b) a second insertion tool arm configured to travel along a second arcuate path to drive the second anchor along the second channel, and (c) a lever operatively coupled to the first and second insertion tool arms;
wherein the first and second insertion tool arms are configured to respectively travel along the first and second arcuate paths simultaneously with one another in response to movement of the lever.

20. The system of claim 19 wherein a horizontal axis intersects the lateral wall, the resilient member, and the first and second channels.

\* \* \* \* \*